(12) United States Patent
Vulto et al.

(10) Patent No.: US 11,629,319 B2
(45) Date of Patent: Apr. 18, 2023

(54) CELL CULTURE DEVICE AND METHODS

(71) Applicant: Mimetas B.V., DH Oegstgeest (NL)

(72) Inventors: Paul Vulto, DH Oegstgeest (NL); Sebastiaan Johannes Trietsch, DH Oegstgeest (NL); Arnaud Nicolas, DH Oegstgeest (NL)

(73) Assignee: Mimetas, B.V., DH Oegstgeest (NL)

( * ) Notice: Subject to any disclaimer, the term of this patent is extended or adjusted under 35 U.S.C. 154(b) by 1015 days.

(21) Appl. No.: 16/309,298

(22) PCT Filed: Jun. 12, 2017

(86) PCT No.: PCT/EP2017/064302
§ 371 (c)(1),
(2) Date: Dec. 12, 2018

(87) PCT Pub. No.: WO2017/216113
PCT Pub. Date: Dec. 21, 2017

(65) Prior Publication Data
US 2020/0063081 A1 Feb. 27, 2020

(30) Foreign Application Priority Data

Jun. 15, 2016 (NL) .................................... 2016965
Dec. 21, 2016 (NL) .................................... 2018033

(51) Int. Cl.
*C12M 3/06* (2006.01)
*B01L 3/00* (2006.01)
(Continued)

(52) U.S. Cl.
CPC ....... *C12M 23/16* (2013.01); *B01L 3/502715* (2013.01); *C12M 21/08* (2013.01);
(Continued)

(58) Field of Classification Search
None
See application file for complete search history.

(56) References Cited

U.S. PATENT DOCUMENTS

| 4,829,000 A | 5/1989 | Kleinman et al. |
| 9,243,221 B2 | 1/2016 | Yarmush et al. |

(Continued)

FOREIGN PATENT DOCUMENTS

| CN | 102257124 A | 11/2011 |
| CN | 104877905 A | 9/2015 |

(Continued)

OTHER PUBLICATIONS

Date et al., "Mini-Gut Organoids: Reconstitution of the Stem Cell Niche", Annual Review of Cell and Developmental Biology, Sep. 25, 2015, pp. 32.1-32.21.

(Continued)

*Primary Examiner* — William H. Beisner
(74) *Attorney, Agent, or Firm* — Offit Kurman, P.A.; Gregory A. Grissett

(57) ABSTRACT

A method of vascularising a cell aggregate on a microfluidic device, microfluidic cell culture devices comprising perfusable vascular networks and kits and assays using the microfluidic cell culture devices are described. The microfluidic devices comprise one or more capillary pressure barriers allowing for formation of an extracellular matrix gel within a confined area of the network, in which cells can be cultured for different uses.

20 Claims, 20 Drawing Sheets

(51) Int. Cl.
 C12M 3/00 (2006.01)
 C12M 1/00 (2006.01)
 C12N 5/071 (2010.01)
(52) U.S. Cl.
 CPC ........... C12M 23/38 (2013.01); C12N 5/0691 (2013.01); *B01L 3/5027* (2013.01); *B01L 2300/041* (2013.01); *B01L 2300/0858* (2013.01); *C12N 2501/999* (2013.01); *C12N 2506/28* (2013.01); *C12N 2531/00* (2013.01); *C12N 2533/30* (2013.01)

(56) References Cited

U.S. PATENT DOCUMENTS

| | | | | |
|---|---|---|---|---|
| 2007/0264705 | A1* | 11/2007 | Dodgson | C12M 23/12 435/283.1 |
| 2011/0117634 | A1* | 5/2011 | Halamish | C12M 23/16 435/283.1 |
| 2011/0287982 | A1* | 11/2011 | Stoppini | C12M 25/01 506/40 |
| 2014/0065597 | A1 | 3/2014 | Vulto et al. | |
| 2014/0335496 | A1 | 11/2014 | Grego et al. | |
| 2014/0348706 | A1* | 11/2014 | Rahman | G01N 33/4836 422/502 |
| 2015/0238952 | A1 | 8/2015 | Vulto et al. | |
| 2015/0377861 | A1 | 12/2015 | Pant et al. | |

FOREIGN PATENT DOCUMENTS

| | | |
|---|---|---|
| EP | 2213364 A1 | 8/2010 |
| EP | 2422909 | 2/2012 |
| EP | 2622342 | 8/2013 |
| EP | 2811013 A1 | 12/2014 |
| JP | 2011510656 A | 4/2011 |
| RU | 2584598 C1 | 5/2016 |
| WO | 2007008609 A2 | 1/2007 |
| WO | 2008079320 A1 | 7/2008 |
| WO | 2009097247 A1 | 8/2009 |
| WO | 2009146911 A2 | 12/2009 |
| WO | 2010031194 A1 | 3/2010 |
| WO | 2010086179 A2 | 8/2010 |
| WO | 2010149292 A1 | 12/2010 |
| WO | 2012050981 A1 | 4/2012 |
| WO | 2012118799 A2 | 9/2012 |
| WO | 2012120101 A1 | 9/2012 |
| WO | 2013085909 A1 | 6/2013 |
| WO | WO 2013/085909 * | 6/2013 |
| WO | 2013151616 A1 | 10/2013 |
| WO | 2014038943 A1 | 3/2014 |
| WO | 2015032889 A1 | 3/2015 |
| WO | 2015138032 A2 | 9/2015 |
| WO | 2016077277 A1 | 5/2016 |
| WO | 2016081751 A1 | 5/2016 |
| WO | 2016186503 A1 | 11/2016 |
| WO | 2016195480 A1 | 12/2016 |

OTHER PUBLICATIONS

Deosarkar et al., "A Novel Dynamic Neonatal Blood-Brain Barrier on a Chip", PLOS ONE | DOI:10.1371/journal.pone.0142725, Nov. 10, 2015, 21 pp.
Giese et al., "Immunological substance testing on human lymphatic micro-organoids in vitro", Journal of Biotechnology, vol. 148, 2010, pp. 38-45.
Hayashi et al., "Vascular network formation for a long-term spheroid culture by co-culturing endothelial cells and fibroblasts", 28th IEEE International Conference on Micro Electro Mechanical Systems (MEMS), Estoril, Portugal, Jan. 18-22, 2015, pp. 476-479.
Officer Nora Lindner, International Preliminary Report on Patentability, International Patent Application No. PCT/EP2017/064302, dated Dec. 18, 2018, 10 pp.
Officer Jose Cubas Alcaraz, International Search Report and the Written Opinion, International Patent Application No. PCT/EP2017/064302, dated Dec. 7, 2017, 15 pp.
Kim et al., "Engineering of functional, perfusable 3D microvascular networks on a chip, Lab Chip", Royal Society of Chemistry Publishing, 13, 2013, pp. 1489-1500.
Lancaster et al., "Cerebral organoids model human brain development and microcephaly", Europe OMC Funders Group, DOI: 10.1038/nature 12517, Nature, Sep. 19, 2013, 21 pp.
Lee et al., "Hydrogels for Tissue Engineering", Chemical Reviews, vol. 101, No. 7, Jul. 2001, pp. 1869-1879.
Muira et al., "Tissue culture on a chip: Developmental biology applications of self-organized capillary networks in microfluidic devices", Development, Growth and Differentiation, 58, 2016, pp. 505-515.
Moreno et al., "Differentiation of neuroepithelial stem cells into functional dopaminergic neurons in 3D microfluid cell culture". The Royal Society of Chemistry, Lab on a Chip, vol. 15, No. 1, 2015, pp. 2419-2428.
Pampaloni et al., "The third dimension bridges the gap between cell culture and live tissue", Nature Reviews Molecular Biology, AOP, DOI: 10.1038/nrm 2236, Aug. 8, 2007, 7 pp.
Russian Office Action with English translation and Russian Search Report, Related Russian Patent Application No. 2019100603/10(000981), dated Aug. 12, 2020, 8 pp.
Shattil et al., "Adhesive signaling in platelets", Current Opinion in Cell Biology, Current Biology, Ltd., vol. 6, 1994, pp. 695-704.
Sonntag et al., "Design and prototyping of a chip=based multi-micro-organoid culture system for substance testing, predictive to human (substance) exposure", Journal of biotechnology, 148:1 (2010) 70-75.
Takasato et al., "Kidney organoids from human iPS cells contain multiple lineages and model human nephrogenesis", Nature, vol. 526, Oct. 22, 2015, 22 pp.
Vulto et al., "Phaseguides: a paradigm shift in microfludic priming and emptying", The Royal Society of Chemistry, Lab on a Chip, vol. 11, No. 9, May 7, 2011, pp. 1561-1700.
Taunk, Dr. Kavita, Examination Report, Intellectual Property Office India, Corresponding Indian Patent Application 201917001511, dated Dec. 11, 2020, 6 pp.
Formalities Officer: Debora Dupke, European Patent Office Action, Co-Pending European Patent Application No. 2017732721, dated May 19, 2021, 6 pp.
Formalities Officer: Cornelia Schulze, Third Party Observation for European Patent Application No. 2017732721, Feb. 17, 2021, 4 pp.
Formalities Officer: Cornelia Schulze, Third Party Observation for European Patent Application No. 2017732721, Feb. 19, 2021, 37pp.
Formalities Officer: Doreen Golze, Third Party Observation for European Patent Application No. 2017732721, Feb. 24, 2021, 5 pp.
Counterpart Brazil Office Action, Brazil Patent Application No. BR112018075920-1, dated Nov. 17, 2021, 5 pp.
Moreno et al., "Differentiation of neuroepithelial stem cells into functional dopaminergic neurons in 3D microfluidic cell culture", Lab on a Chip, The Royal Society of Chemistry, vol. 15, No. 11, ISSN 1473-0197, pp. 2419-2428, http://dx.doi.org/10.1039/C5LC00180C.
Vulto et al., "Phaseguides: a paradigm shift in microfluidic priming and emptying", Lab on a Chip, The Royal Society of Chemistry, vol. 11, No. 9, ISSN 1473-0197, Feb. 16, 2011, 7 pp., http://dx.doi.org/10.1039/c0lc00643b.
Filed by Michael Ponomarenko, Third Party Observations for European Patent Application EP20170732821, Observations Filed Sep. 20, 2021, 89 pp.
Formalities Officer: Doreen Golze, Third Party Observations of European Patent Application 17732821.8, Nov. 5, 2021, 8 pp.
Formalities Officer: Doreen Golze, Third Party Observations of European Patent Application 17732821.8, Nov. 8, 2021, 100 pp.

* cited by examiner

CELL CULTURE DEVICE AND METHODS

CROSS-REFERENCE TO RELATED APPLICATIONS

This application is a National Stage Application filed under 35 U.S.C. 371 of International Application No. PCT/EP2017/064302, filed Jun. 12, 2017, which claims priority to Netherlands Patent Application 2016965, filed Jun. 15, 2016 and Netherlands Patent Application No. 2018033, filed Dec. 21, 2016, the contents of which are hereby incorporated by reference as set forth in their entirety herein.

FIELD OF THE INVENTION

The present invention relates to a method of a device for 3D culture of cells, for example a multi-well plate allowing for a controlled and reliable vascularization and/or perfusion of organoid assays and/or cell cultures. It equally provides methods for generation of 3D cultured cells and for vascularization/perfusion of the cultured cells, and assay plates and uses thereof resulting from the device and methods.

BACKGROUND TO THE INVENTION

In a drive towards ever better predictive phenotypic models for drug testing and disease mimicking, progress has been made in recent years in the field of organoid culture. An organoid is a three-dimensional organ-bud that typically comprises most specialized cells that are also available in the human body. In practice, the culture and differentiation of tissue during embryonic regenerative development is mimicked in an in vitro environment, such that stem cells differentiate to various differentiated cells.

A well-known example of such organoids are the small intestinal organoids (Shoichi Date and Toshiro Sato, Mini-Gut Organoids: Reconstitution of the Stem Cell Niche, Annu. Rev. Cell Dev. Biol., 2015, Vol. 31: 269-289). A cocktail of growth factors and signaling molecules such as Wnt pathway agonists (e.g. Wnt3a, R-spondin, CHIR99021), BMP/TGF pathway inhibitors (e.g. Noggin), EGF and an environment of basement membrane extract (matrigel or similar), assures culture of primary gut crypts, maintenance of its stem cell niche and potential of differentiation of cells towards for example goblet cells, enterocytes and enteroendocrine cells. This leads to a three-dimensional structure having secondary morphology aspects of the gut, including crypt and villus formation. Similar three-dimensional cultures have been established for the culture of primary human esophageal, gastric, colon, liver and pancreatic.

More recently, progress has been made on growing brain organoids from induced pluripotent stem cells. Long term culture of suspended spheroids under continuous shaking leads to so-called minibrains with specialized sections such as fore- and hindbrain characteristics [Cerebral organoids model human brain development and microcephaly, M. A. Lancaster, et al. Nature 2013, 501, 373-379]. Even more recently, a breakthrough has been realized in the culture of the kidney glomerulus, using a complex culture protocol, starting with induced pluripotent stem cells on transwell systems, that lead again to highly specialized cells that are present in the glomeruli of human kidneys [Kidney organoids from human iPS cells contain multiple lineages and model human nephrogenesis, M. Takasato et al., Nature 2015, 526, 564-568].

Organoid culture, or more generally speaking 3D cell culture can be performed in a variety of manners. 3D spheroids can be formed in so-called hanging drop plates (see for instance WO 2010/031194) or low adhesion microtiter plates. Although it is claimed that these spheroids have significantly improved predictivity to standard cell cultures, it is not used for most organoid cultures. The reason is that organoids typically require an extracellular matrix component, such as Matrigel, or collagen that is not present in the hanging drop or low adhesion plate spheroids. Parallel efforts led to the development of 3D cell-culture models in which cells are grown embedded in an extracellular matrix. This approach enhances expression of differentiated functions and improves tissue organization (Pampaloni et al. (2007). Nat Rev Mol Cell Biol 8: 839-84).

Typical platforms to grow organoids comprise standard petri dishes, micro titre plates and in some cases Transwell® plates from Corning. In these cases the organoids are grown in an extracellular matrix (ECM) or on an ECM coated well. As already addressed above these organoids lack the presence of vasculature, thus limiting their growth as beyond a certain size hypoxic and in a later stage necrotic cores may be formed. Also it is hypothesised that the presence of endothelium is crucial for the development towards a physiological relevant tissue, as the endothelium excretes important factors for the target tissue.

Microfluidic cell culturing is an increasingly important technology, finding use in drug screening, tissue culturing, toxicity screening, and biologic research.

Numerous microfluidic systems, devices, methods and manufacturing are known, including patent documents such as WO 2008/079320, WO 2013/151616, WO 2010/086179, WO2012/120101, or as commercially available from, for example, Mimetas, Leiden, The Netherlands (e.g. Organo-Plate; www.mimetas.com). While no particular limitations should be read from those applications and documents into any claims presented herein, these documents provide useful background material.

In *A Novel Dynamic Neonatal Blood-Brain Barrier on a Chip*. S. Deosarkar, B. Prabhakarpandian, B. Wang, J. B. Sheffield, B. Krynska, M. Kiani. *PLOS ONE*, 2015 a microfluidic device was developed to generate vasculature and used a sieving like structure to separate the endothelium from astrocytes in an attempt to generate a blood-brain barrier type structure. In WO 2007/008609 A2 a similar sieve like structure is used to form cell aggregates in order to create a tissue morphology that is better mimicking e.g. the physiology of a liver.

None of the above examples of microfluidic cell culture allows for culture of organoids in an ECM with distinct vasculature that can be perfused.

The progress of growing organoids and embryonic bodies, is hampered by lack of technical means to support this growth. The culture techniques are highly cumbersome and may vary greatly from organ to organ. A standard device is needed that is preferably harmonized with the current standard of multiwell titreplate. Second, perfusion flow or agitation appears to be crucial for such organoids to grow beyond a certain size, as dense clumps of cells need oxygen rich, nutrient rich media in order to prevent necrotic cores. Third, the extracellular matrix (ECM) can be a crucial factor for correct differentiation, but culture protocols are not all compatible with ECM gel culture. Most importantly of all, so far the growth of embryonic bodies and organoids has been strongly limited by lack of vasculature. This limits the maximum size of the organoids.

There accordingly remains a need for a system that allows perfused culture of ECM supported organoids or embryonic bodies that preferably enables vascularization of the organoid and perfusion of the vasculature. The platform should be also compatible with current-day readout and handling equipment.

It has been an object of the present invention to address some or all of the above mentioned needs.

SUMMARY OF THE INVENTION

According to a first aspect of the present invention, there is provided a cell culture device comprising a microfluidic network, the microfluidic network comprising:
- a microfluidic layer comprising a base, a microfluidic channel and a cover;
- an organoid compartment extending into the microfluidic layer through an aperture in the cover and in fluid communication with the microfluidic channel; and
- a capillary pressure barrier substantially aligned with the aperture and dividing the microfluidic network into a first sub-volume comprising the organoid compartment and a second sub-volume comprising at least a part of the microfluidic channel.

According to a second aspect of the present invention, there is provided a method for culturing cells or cell aggregates, comprising:
a) introducing into the organoid compartment of a device of the first aspect a droplet of a gel or gel-precursor optionally comprising one or more types of cells or cell aggregates;
b) allowing the droplet to be confined by the capillary pressure barrier;
c) allowing the droplet of gel or gel-precursor to cure or gelate;
d) loading the microfluidic channel with a fluid; and
e) optionally culturing the one or more type of cells or cell aggregates present in the cured gel.

According to a third aspect of the present invention, there is provided an assay plate, comprising the device of the first aspect provided with a gel confined by the capillary pressure barrier to the organoid compartment, wherein the gel comprises one or more cells or cell aggregates.

According to a fourth aspect of the present invention, there is provided a kit, comprising:
the assay plate of the third aspect of the invention; and
one or more pro-angiogenic compounds, for inducing angiogenesis.

According to a fifth aspect of the present invention, there is provided a method of vascularising a cell aggregate, comprising:
introducing into a microfluidic cell culture device a droplet of a gel or gel-precursor and allowing the droplet to be confined by a capillary pressure barrier present in the device;
allowing the gel or gel-precursor to cure or gelate to form a cured gel;
introducing a suspension of endothelial cells in a carrier fluid into a microfluidic channel of the microfluidic cell culture device, the microfluidic channel being in fluid communication with the cured gel;
allowing the endothelial cells to form at least one microvessel in at least the microfluidic channel;
introducing onto a top surface of the cured gel one or more cells or cell aggregates; and
allowing or promoting directional angiogenesis between the at least one microvessel and the one or more cells or cell aggregates.

According to a sixth aspect of the present invention, there is provided a microfluidic cell culture device comprising a perfusable vascular network, the vascular network comprising:
a microfluidic channel having an inlet and an outlet;
an extracellular matrix gel arranged to receive at least one cell to be vascularised on a top surface thereof;
wherein the microfluidic channel is in fluid communication with the extracellular matrix gel and comprises a vascular network of endothelial cells lining the internal surfaces of the microfluidic channel.

According to a seventh aspect of the present invention, there is provided a microfluidic cell culture device, comprising:
a microfluidic channel having an inlet and an outlet;
an extracellular matrix having a biological tissue disposed on a top surface thereof;
wherein the microfluidic channel comprises a vascular network of endothelial cells lining the internal surfaces of the microfluidic channel and extending through the extracellular matrix to the biological tissue.

According to a eighth aspect of the present invention, there is provided a kit, comprising:
the microfluidic cell culture device of the sixth or the seventh aspects of the invention; and
one or more pro-angiogenic compounds, for inducing angiogenesis.

Various other aspects of the present invention relate to uses of the first, third, fourth, and sixth to eighth aspects.

Definitions

Various terms relating to the devices, methods, uses and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

As used herein, the "a," "an," and "the" singular forms also include plural referents unless the content clearly dictates otherwise. Thus, for example, reference to 'a cell' includes a combination of two or more cells, and the like.

As used herein, "about" and "approximately": these terms, when referring to a measurable value such as an amount, a temporal duration, and the like, are meant to encompass variations of ±20% or ±10%, more preferably ±5%, even more preferably ±1%, and still more preferably ±0.1% from the specified value, as such variations are appropriate to perform the disclosed methods.

As used herein, "comprising" is construed as being inclusive and open ended, and not exclusive. Specifically, the term and variations thereof mean the specified features, steps or components are included. These terms are not to be interpreted to exclude the presence of other features, steps or components.

As used herein, "exemplary" means "serving as an example, instance, or illustration," and should not be construed as excluding other configurations disclosed herein.

As used herein, the term "microfluidic channel" refers to a channel on or through a layer of material that is covered by a top-substrate or cover, with at least one of the dimensions of length, width or height being in the sub-millimeter range. It will be understood that the term encompasses channels which are linear channels, as well as channels which are branched, or have bends or corners within their path. A microfluidic channel typically comprises an inlet for administering a volume of liquid. The volume enclosed by a microfluidic channel is typically in the microliter or sub-microliter range. A microfluidic channel typically comprises a base, which may be the top surface of an underlying material, two side walls, and a ceiling, which may be the lower surface of a top substrate overlying the microfluidic channel, with any configuration of inlets, outlets and/or vents as required.

As used herein, "droplet retention structures", and "capillary pressure barriers" are used interchangeably, and are used in reference to features of a device that keep a liquid-air meniscus pinned on a certain position by capillary forces.

As used herein, with particular reference to capillary pressure barriers, a "closed geometric configuration" is one in which the capillary pressure barrier is other than a linear capillary pressure barrier with two ends and instead forms a closed loop. For example, when viewed from above, a capillary pressure barrier with a closed geometric configuration may comprise a circular capillary pressure barrier, or a polygonal capillary pressure barrier, for example a triangular capillary pressure barrier, or a square capillary pressure barrier, or a pentagonal capillary pressure barrier, and so on.

As used herein, the term "concentric" is to be understood as referring to any closed geometric configuration of the capillary pressure barrier and not solely to a circular configuration.

As used herein, a "linear" capillary pressure barrier is not to be construed as being a straight line, but is instead to be construed as being other than a closed geometric configuration, i.e. as a line with two ends, but which may comprise one or more bends or angles. A linear capillary pressure barrier typically intersects at each end with a side-wall of the microfluidic channel.

As used herein, the term "endothelial cells" refers to cells of endothelial origin, or cells that are differentiated into a state in which they express markers identifying the cell as an endothelial cell.

As used herein, the term "epithelial cells" refers to cells of epithelial origin, or cells that are differentiated into a state in which they express markers identifying the cell as an epithelial cell.

As used herein, the term "droplet" refers to a volume of liquid that may or may not exceed the height of the microfluidic channel and does not necessarily represent a round, spherical shape. Specifically, references to a gel droplet are to a volume of gel in the organoid compartment.

As used herein, the term "biological tissue" refers to a collection of identical, similar or different types of functionally interconnected cells that are to be cultured and/or assayed in the methods described herein. The cells may be a cell aggregate, or a particular tissue sample from a patient. For example, the term "biological tissue" encompasses organoids, tissue biopsies, tumor tissue, resected tissue material and embryonic bodies.

As used herein, the term "cell aggregate" refers to a 3D cluster of cells in contrast with surface attached cells that typically grow in monolayers. 3D clusters of cells are typically associated 35 with a more in-vivo like situation. In contrast, surface attached cells may be strongly influenced by the properties of the substrate and may undergo de-differentiation or undergo transition to other cell types.

As used herein, the term "organoid" refers to a miniature form of a tissue that is generated in vitro and exhibits endogenous three-dimensional organ architecture.

As used herein, the term "transplant" or "transplantation" refers to the transfer of tissue, for example tissue explant, or cell aggregates from one location to another, for example from a storage container to a cell culture device.

BRIEF DESCRIPTION OF THE FIGURES

The present invention will now be described by way of example only, with reference to the Figures, in which.

Figure 1:
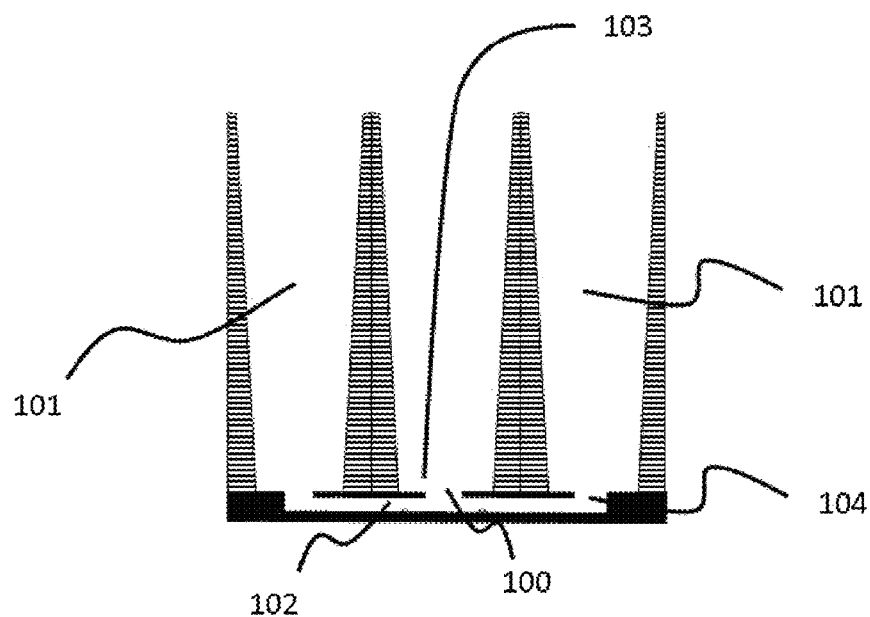
FIGS. 1 to 3 show a vertical cross-section view (FIG. 1), a horizontal top view (FIG. 2), and a close up vertical cross-section view (FIG. 3) of a first possible configuration for a microfluidic network as used in a device according to the present invention.

With specific reference to the Figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention.

Cell Culture Device

A cell culture device is described. The cell culture device is preferably in a multi-array format/multi-well format to enable its use in in-vitro cell-based assays, pharmaceutical screening assays, toxicity assays, and the like; in particular in a high-throughput screening format. Such multi-well culture plates are available in 6-, 12-, 24-, 48-, 96-, 384- and 1536 sample wells arranged in a rectangular matrix, wherein in the context of the present invention a multi-array configuration of microfluidic networks as herein described are present in the cell culture device. In one example, the cell culture device is compatible with one or more dimensions of the standard ANSI/SLAS microtiter plate format.

The cell culture device therefore preferably has a plurality of microfluidic networks as herein described. In one example, the plurality of microfluidic networks are fluidly connected to each other through the microfluidic layer (which is as described herein). In another example, the plurality of microfluidic networks are fluidly disconnected from each other; in other words, each microfluidic network operates independently of any other microfluidic network present on the cell culture device.

In one example, the cell culture device comprises a microfluidic network, the microfluidic network comprising:
  a microfluidic layer comprising a base, a microfluidic channel and a cover;
  an organoid compartment extending into the microfluidic layer through an aperture in the cover and in fluid communication with the microfluidic channel; and
  a capillary pressure barrier substantially aligned with the aperture and dividing the microfluidic network into a first sub-volume comprising the organoid compartment and a second sub-volume comprising at least a part of the microfluidic channel.

In one example, the cell culture device is a microfluidic cell culture device comprising a perfusable microfluidic or vascular network, the vascular network comprising:
  a microfluidic channel having an inlet and an outlet;
  an extracellular matrix gel arranged to receive at least one cell to be vascularised on a top surface thereof;
  wherein the microfluidic channel is in fluid communication with the extracellular matrix gel and comprises a vascular network of endothelial cells lining the internal surfaces of the microfluidic channel.

In one example, the extracellular matrix gel is arranged to receive a suspension of cells or one or more cell aggregates.

In one example, the cell culture device is a microfluidic cell culture device, comprising:
  a microfluidic channel having an inlet and an outlet;
  an extracellular matrix having a biological tissue disposed on a top surface thereof;
  wherein the microfluidic channel comprises a vascular network of endothelial cells lining the internal surfaces of the microfluidic channel and extending through the extracellular matrix to the biological tissue.

In one example, the microfluidic channel is in fluid communication with the extracellular matrix.

Generally, the cell culture device is a microfluidic cell culture device that comprises at least a microfluidic channel. Different configurations of microfluidic channels or networks are possible within the metes and bounds of the invention, but may include for example a volume or sub-volume within or in fluid communication with the microfluidic channel, for receiving and confining a gel, for example an extracellular matrix.

The or each microfluidic network of one example of the cell culture device generally comprises a microfluidic layer; an organoid compartment and a capillary pressure barrier, each of which will now be described in detail.

Microfluidic Layer

The microfluidic layer of the microfluidic network comprises a base, a microfluidic channel and a cover, also referred to herein as a cover layer, and can be fabricated in a variety of manners.

A typical method of fabrication is to cast a mouldable material such as polydimethylsiloxane onto a mould, so imprinting the microfluidic channel into the silicon rubber material. The rubber material with the channel embedded is subsequently placed on a base layer of glass or of the same material to thus create a seal. Alternatively, the channel structure could be etched in a material such as glass or silicon, followed by bonding to a top or bottom substrate (also referred to herein as a base layer and cover layer). Injection moulding or embossing of plastics followed by bonding is another manner to fabricate the microfluidic channel network. Using yet another technique for fabricating the microfluidic channel network is by photo lithographically patterning the microfluidic channel network in a photopatternable polymer, such as SU-8 or various other dry film or liquid resists, followed by a bonding step. When referred to bonding it is meant the closure of the channel by a top or bottom substrate. Bonding techniques include anodic bonding, solvent bonding adhesive bonding, and thermal bonding amongst others.

The base, also referred to herein as the base layer, or bottom substrate, is preferably formed from a rigid material, such as glass, and serves to provide a supporting surface for the rest of the microfluidic network. In one example, the base is of the same or similar dimensions to the well area of a standard ANSI/SLAS microtitre plate.

As deduced from the various fabrication methods above, the microfluidic layer may comprise a sub-layer comprising a microfluidic channel disposed on the base layer, or is patterned in either the cover or base layer. In an in use orientation, the microfluidic sub-layer is disposed on the top surface of the base layer. The microfluidic channel may be formed as a channel through a sub-layer of material disposed on the base layer. In one example, the material of the sub-layer is a polymer placed on the base layer and into which the microfluidic channel is patterned. In some examples, the microfluidic layer comprises two or more microfluidic channels, which may be in fluidic communication with each other via the organoid compartment.

The microfluidic layer comprises a cover or cover layer covering the microfluidic channel. The cover or cover layer can be formed from any suitable material as is known in the art, for example a glass layer bonded to the sub-layer comprising the microfluidic channel. In one example, the cover layer is provided with pre-formed holes or apertures at defined points. The apertures allow for fluid communication between the microfluidic channel of the microfluidic layer and other components of the microfluidic network disposed thereon.

The microfluidic channel may be provided with one or more inlets, and one or more outlets or vents, as required for any particular use of the microfluidic network of the cell culture device. In order to allow filling, emptying and perfusion of a fluid through the microfluidic network, the microfluidic channel is preferably provided with at least one inlet and at least one outlet or vent. In one example, each of the at least one inlet and at least one outlet or vent is preferably formed as, or so as to be in fluid communication with, a pre-formed aperture in the cover layer.

Organoid Compartment

In one embodiment, the microfluidic network of the cell culture device comprises an organoid compartment extending into the microfluidic layer through an aperture in the cover and in fluid communication with the microfluidic channel. The organoid compartment may be at least partially present in a separate layer to the microfluidic layer. In an in use orientation, the organoid compartment may be at least partially present in a separate layer disposed on the cover of the microfluidic layer, for example a user interface layer comprising a bottomless well as described below.

The organoid compartment comprises a volume of the microfluidic network and is defined in part as a cavity or well which is capable of receiving a droplet of a fluid. In one example, the organoid compartment is provided with an inlet, or an opening at its top end (with reference to an in use orientation), through which it is capable of receiving fluids.

In one example, the organoid compartment comprises a bottomless well of the type found on some microtitre plates, with the well having sidewalls that, in an in use orientation, extend downwardly to the aperture of the cover. Thus, in one example, the organoid compartment comprises a well with downwardly extending side walls so that the organoid compartment extends into the microfluidic layer through the aperture of the cover.

In one example, the well may be an extension of the aperture in the cover layer or a dedicated well structure on top of the cover layer. In a typical embodiment, the well is present as one of a microtiter plate with, for example a square, a rectangular or a circular cross-section. In one example, the internal cross-sectional dimensions of the well correspond substantially to the cross-sectional dimensions of the aperture of the cover layer. In one example, the downwardly extending walls of the well are aligned with the aperture of the cover layer. In one example, the aperture of the cover layer is narrower than the internal dimensions of the well. In one example, the aperture of the cover layer is larger than the internal dimensions of the well. In one example, the organoid compartment is defined in part by the downwardly extending walls of the well terminating in the aperture and in part by the presence of a capillary pressure aligned with the aperture, as is described herein.

The organoid compartment preferably has a certain minimum volume, in order to receive and retain a droplet, of more than 1 microliter, preferably more than 5 microliters and more preferably more than 10 microliters. In a further embodiment, the volume encompassed by the organoid compartment is larger than the volume of a liquid composition to be introduced, in order to further be able to retain additional growth medium, reagents, compounds, or chemoattractants, for example. In one example, the organoid compartment will thus encompass a volume of more than 10 microliters, preferably more than 50 microliters and even more preferably more than 100 microliters.

In one example, the lower portion of the organoid compartment is present in the microfluidic layer, in fluid communication with the microfluidic channel. The lower portion of the organoid compartment may be defined at least in part by the presence of a capillary pressure barrier. The capillary pressure barrier may be disposed on an internal surface of the microfluidic channel as herein described. In one example, the organoid compartment intersects the microfluidic channel through the presence of the capillary pressure barrier on an internal surface of the microfluidic channel. In one example, the organoid compartment is defined in part by a well having downwardly extending sidewalls, and in part by a volume of the microfluidic network defined in part by the capillary pressure barrier, which will now be described.

Capillary Pressure Barrier

The microfluidic network of the cell culture device comprises a capillary pressure barrier substantially aligned with the aperture in the cover layer and dividing the microfluidic network into a first sub-volume comprising the organoid compartment and a second sub-volume comprising at least a part of the microfluidic channel.

The function and patterning of capillary pressure barriers have been previously described, for example in WO 2014/038943 A1. As will become apparent from the exemplary embodiments described hereinafter, the capillary pressure barrier, also referred to herein as a droplet retention structure, is not to be understood as a wall or a cavity which can for example be filled with a droplet comprising one or more cells or cell aggregates, but consists of or comprises a structure which ensures that such a droplet does not spread due to the surface tension. This concept is referred to as meniscus pinning. As such, stable confinement of a droplet comprising one or more cells or cell aggregates, to the organoid compartment of the cell culture device can be achieved. In one example, the capillary pressure barrier may be referred to as a confining phaseguide, which is configured to not be overflown during normal use of the cell culture device. The nature of the confinement of a droplet is described later in connection with the description of the methods of the present invention.

In one example, the capillary pressure barrier comprises or consists of a rim or ridge of material protruding from an internal surface of the microfluidic channel; or a groove in an internal surface of the microfluidic channel. The sidewall of the rim or ridge may have an angle α with the top of the rim or ridge that is preferably as large as possible. In order to provide a good barrier, the angle α should be larger than 70°, typically around 90°. The same counts for the angle α between the sidewall of the ridge and the internal surface of the microfluidic channel on which the capillary pressure barrier is located. Similar requirements are placed on a capillary pressure barrier formed as a groove.

An alternative form of capillary pressure barrier is a region of material of different wettability to an internal surface of the microfluidic channel, which acts as a spreading stop due to capillary force/surface tension. As a result, the liquid is prevented from flowing beyond the capillary pressure barrier and enables the formation of stably confined volumes in the organoid compartment. In one example, the internal surfaces of the microfluidic channel comprise a hydrophilic material and the capillary pressure barrier is a region of hydrophobic, or less hydrophilic material. In one example, the internal surfaces of the microfluidic channel comprise a hydrophobic material and the capillary pressure barrier is a region of hydrophilic, or less hydrophobic material.

Thus in a particular embodiment of the present invention, the capillary pressure barrier is selected from a rim or ridge, a groove, a hole, or a hydrophobic line of material or combinations thereof. In another embodiment capillary pressure barriers can be created by pillars at selected intervals, the arrangement of which defines the first sub-volume or area that is to be occupied by the gel. In one example, the pillars extend the full height of the microfluidic channel.

The capillary pressure barrier is substantially aligned with the aperture in the cover layer so as to restrict spread of a droplet of fluid within the microfluidic network. In one example, the capillary pressure barrier is located on an underside of the cover layer substantially adjacent the aperture. In one example, the capillary pressure barrier is formed at least in part by the aperture itself.

In one example, the capillary pressure barrier is provided on an internal surface of the microfluidic channel facing the aperture in the cover. In a more particular embodiment the capillary pressure barrier is present on the base of the microfluidic layer or on the internal surface of the microfluidic channel substantially opposite or facing the aperture. In one example, the capillary pressure barrier is positioned underneath the well or underneath the walls of the well of the organoid compartment in an in use orientation. In one example, the capillary pressure barrier is present as previously defined in relation to the aperture or well in order to confine a droplet of fluid to the region of the microfluidic layer aligned with the aperture and/or the well of the organoid compartment.

In one example, the capillary pressure barrier defines at least in part a surface of the organoid compartment on the base of the microfluidic layer or on the base of the microfluidic channel. The capillary pressure barrier is configured to confine a fluid to the first sub-volume comprising the organoid compartment. In one example, the capillary pressure barrier comprises a closed geometric configuration. In one example, the capillary pressure barrier is concentric with the aperture of the cover layer.

In one example, the diameter or area defined by the circumference of the capillary pressure barrier is greater than the diameter or area defined by the circumference of the aperture; in other words the capillary pressure barrier is circumferential to and larger than the aperture. In another example, the diameter or area defined by the circumference of the aperture is greater than the diameter or area defined by the circumference of the capillary pressure barrier; in other words the aperture is circumferential to and larger than the capillary pressure barrier. Irrespective of the shape, in a preferred embodiment the capillary pressure barrier delineates the contact area of a droplet of liquid or gel composition comprising one or more cells or cell aggregates introduced into the well of the organoid compartment with the base of the organoid compartment, i.e. being circumferential to the contact area of the droplet comprising one or more cells or cell aggregates with the base of the organoid compartment.

In one example, the capillary pressure barrier is a substantially linear capillary pressure barrier which spans the complete width of the microfluidic channel and intersects on each end with sidewalls of the microfluidic channel.

As part of the microfluidic network, the capillary pressure barrier divides the network into at least two sub-volumes, one of said sub-volumes comprising the organoid compartment in which an organoid body is cultured and the other sub-volume comprising the microfluidic channel connecting the organoid compartment to the rest of the microfluidic network.

Second Capillary Pressure Barrier

In some examples, the microfluidic network of the cell culture device is provided with a second capillary pressure barrier, the form and function of which is substantially as described above. For the avoidance of doubt, references to "a capillary pressure barrier" are to be understood as references to "the first capillary pressure barrier" when a second capillary pressure barrier is present in the device.

In some examples, the second capillary pressure barrier is substantially aligned with the aperture in the cover layer so as to restrict spread of a droplet of fluid within the microfluidic network. In one example, the second capillary pressure barrier is located on an underside of the cover layer substantially adjacent the aperture. In one example, the second capillary pressure barrier is formed at least in part by the aperture itself.

In one example, the second capillary pressure barrier is provided on an internal surface of the microfluidic channel facing the aperture in the cover. In a more particular embodiment the second capillary pressure barrier is present on the base of the microfluidic layer or on the internal surface of the microfluidic channel substantially opposite or facing the aperture. In one example, the second capillary pressure barrier is positioned underneath the well or underneath the walls of the well of the organoid compartment. In one example, the second capillary pressure barrier is present as previously defined in relation to the aperture or well in order to confine a droplet of fluid to the region of the microfluidic layer aligned with the aperture and/or the well of the organoid compartment.

In one example, the second capillary pressure barrier defines at least in part, in combination with the first capillary pressure barrier, a surface of the organoid compartment on the base of the microfluidic layer or on the base of the microfluidic channel. The second capillary pressure barrier is configured, in combination with the first capillary pressure barrier, to confine a fluid to the first sub-volume comprising the organoid compartment. In one example, the second capillary pressure barrier comprises a closed geometric configuration. In one example, the second capillary pressure barrier is concentric with the aperture of the cover layer and/or the first capillary pressure barrier. In one example, the diameter or area defined by the circumference of the second capillary pressure barrier is greater than the diameter or area defined by the circumference of the aperture and/or the first capillary pressure barrier; in other words, the second capillary pressure barrier is circumferential to and larger than the first capillary pressure barrier and/or the aperture. In one example, the second capillary pressure barrier is concentric with the first capillary pressure barrier and is within the circumference of the first capillary pressure barrier. In another example, the diameter or area defined by the circumference of the aperture is greater than the diameter or area defined by the circumference of the second capillary pressure barrier; in other words, the aperture is circumferential to and larger than the second capillary pressure barrier. Irrespective of the shape, in a preferred embodiment the second capillary pressure barrier delineates the contact area of a droplet of a liquid or gel composition comprising one or more cells or cell aggregates introduced into the well of the organoid compartment with the base of the organoid compartment, i.e. being circumferential to the contact area of the droplet comprising one or more cells or cell aggregates with the base of the organoid compartment.

In one example, the second capillary pressure barrier is a substantially linear capillary pressure barrier which spans the complete width of the microfluidic channel and intersects on each end with sidewalls of the microfluidic channel. In this example, the first and second capillary pressure barriers may define a cross-sectional area which is aligned with the aperture of the cover layer, and which may also be concentric with the aperture of the cover. In this example, the first capillary pressure barrier can be considered as dividing the microfluidic network into a first sub-volume comprising the organoid compartment and a second sub-volume comprising the microfluidic channel, with the second capillary pressure barrier dividing the microfluidic network into the first sub-volume comprising the organoid compartment and a third sub-volume comprising a second microfluidic channel.

As part of the microfluidic network, the second capillary pressure barrier divides the network into at least two sub-volumes, the first being the first sub-volume referred to previously which comprises the organoid compartment in which an organoid body is cultured, and a third sub-volume. In one example, the third sub-volume comprises a part of the microfluidic channel separate to, i.e. not contained within the first sub-volume. In one example, the third sub-volume is contained entirely within the first-sub volume, i.e. the first and second capillary pressure barriers are both closed geometric configurations and the second capillary pressure barrier is completely encircled by the first capillary pressure barrier.

Reservoir

In some examples, the microfluidic network comprises a reservoir in fluid communication with an inlet to the microfluidic channel. The reservoir may be substantially of the same form or configuration as the well of the organoid compartment, and is present to retain a volume of liquid, for example culture media. In a typical embodiment the reservoir is able to retain a larger volume of fluid than is or can be retained by the microfluidic channel. The reservoir may be an adjacent well to the well of the organoid compartment on a bottomless microtitre plate disposed on top of the microfluidic layer. In other examples, the reservoir may be a well on the same microtitre plate, but spatially distant from the well of the organoid compartment. It will be understood that the proximity of the reservoir to the well of the organoid compartment is not critical to the operation of the cell culture device as long as the two are in fluid communication via the microfluidic layer.

In some examples, the microfluidic network comprises more than one, for example two, or more, reservoirs in fluid communication with the microfluidic layer and with the organoid compartment and any other reservoir present in the microfluidic network. Each reservoir may be in fluid communication with the microfluidic layer via an aperture in the cover layer which may be termed an inlet, or an outlet, of the microfluidic layer as appropriate. In the embodiment in which at least two reservoirs are present in the microfluidic network, a first reservoir may be used for introducing a fluid, for example culture media into the microfluidic network, while the second reservoir may function as a vent, or overflow compartment for receiving the fluid during perfusion, or levelling, as is described below in connection with the methods of the present invention.

In some examples, the microfluidic cell culture device comprises a perfusable microfluidic or vascular network, the vascular network comprising:
 a microfluidic channel having an inlet and an outlet;
 an extracellular matrix gel arranged to receive at least one cell to be vascularised on a top surface thereof;
 wherein the microfluidic channel is in fluid communication with the extracellular matrix gel and comprises a vascular network of endothelial cells lining the Internal surfaces of the microfluidic channel.

In some examples the extracellular matrix gel is arranged to receive a suspension of cells, one or more cell aggregates or a tissue sample. In some examples, the at least one cell to be vascularised comprises a cell aggregate or a biological tissue, as described herein.

In some examples, the cell culture device is a microfluidic cell culture device, comprising:
 a microfluidic channel having an inlet and an outlet;
 an extracellular matrix having a biological tissue disposed on a top surface thereof;
 wherein the microfluidic channel comprises a vascular network of endothelial cells lining the internal surfaces of the microfluidic channel and extending through the extracellular matrix to the biological tissue.

Such devices may also be considered as assay plates due to the presence of the vascular network and the optional biological tissue disposed on a top surface of the extracellular matrix, thus being ready for use in assays or methods described herein. As will be understood from the present disclosure, the production of such devices may be realised using any of the methods described below. In one example, the vascular network of endothelial cells extends into the extracellular matrix gel. Optionally the extensions of vascular network are microvessels that are a result of angiogenesis.

In one example, the biological tissue comprises an organoid, tissue biopsy, tumor tissue, resected tissue material or embryonic body. The biological tissue may comprise one or more epithelial cells and/or cells of mesenchymal origin, or stromal cells, as described below. The biological tissue may optionally also include endothelial cells. The biological tissue may comprise clustered cells, printed cells, an organoid, tissue biopsy, tumor tissue, resected tissue material, organ explant or an embryonic body, depending on the eventual use of the vascularised tissue. The biological tissue may comprise one or more types of cells obtained from, derived from or exhibiting a phenotype associated with a particular tissue or organ, for example liver, kidney, brain, breast, lung, skin, pancreas, intestine, retina or hair. The biological tissue may comprise or be derived from healthy or diseased tissue, and may be obtained from or derived from a patient. The endothelial cells forming the vascular network may be obtained from or derived from a patient, for example the same patient from which the biological tissue has been obtained or derived. In one example, the endothelial cells comprise blood outgrowth endothelial cells (as for instance described in *Nature Protocols* 7, 1709-1715 (2012)) or endothelial cells derived from stem cells, including but not limited to induced pluripotent stem cells.

In one embodiment, the microfluidic channel is disposed in a microfluidic device as described herein. For example, the microfluidic channel may be disposed in a microfluidic layer further comprising a base and a cover. The microfluidic cell culture device may further comprise an organoid compartment extending into the microfluidic layer through an aperture in the cover and in fluid communication with the microfluidic channel; and a capillary pressure barrier substantially aligned with the aperture and dividing the microfluidic network into a first sub-volume comprising the organoid compartment and a second sub-volume comprising at least a part of the microfluidic channel. The extra-cellular matrix gel may be disposed in the organoid compartment and confined thereto by the capillary pressure barrier.

Methods of Culturing Cells or Cell Aggregates

A method for culturing cells or cell aggregates is described. Generally, the method comprises introducing into a microfluidic cell culture device, for example into the organoid compartment of a device as described herein, a droplet of a gel or gel-precursor comprising one or more types of cells or cell aggregates; allowing the droplet to be confined by at least one capillary pressure barrier in the microfluidic cell culture device; allowing the droplet of gel or gel-precursor to cure or gelate; loading a microfluidic channel with a fluid; and culturing the one or more type of cells or cell aggregates present in the cured gel.

In one example of the method, the microfluidic cell culture device is as described herein. In the method, a droplet of a first liquid composition comprising one or more cells or cell aggregates is loaded into the organoid compartment, for example via the opening of a well forming a part of the organoid compartment, and is retained by one or more capillary pressure barriers, and the gel or gel-precursor is allowed to set or gelate. Conditions for forming an extra-cellular matrix gel comprising one or more types of cells or cell aggregates are known in the art, as are conditions for subsequent culture, which will vary depending on the nature of the cells used and the desired outcome.

The gel or gel-precursor includes any hydrogel known in the art suitable for cell culture. Hydrogels used for cell culture can be formed from a vast array of natural and synthetic materials, offering a broad spectrum of mechanical and chemical properties. For a review of the materials and methods used for hydrogel synthesis see Lee and Mooney (Chem Rev 2001; 101(7): 1869-1880). Suitable hydrogels promote cell function when formed from natural materials and are permissive to cell function when formed from synthetic materials. Natural gels for cell culture are typically formed of proteins and ECM components such as collagen, fibrin, hyaluronic acid, or Matrigel, as well as materials derived from other biological sources such as chitosan, alginate or silk fibrils. Since they are derived from natural sources, these gels are inherently biocompatible and bioactive. Permissive synthetic hydrogels can be formed of purely non-natural molecules such as poly(ethylene glycol) (PEG), poly(vinyl alcohol), and poly(2-hydroxy ethyl methacrylate). PEG hydrogels have been shown to maintain the viability of encapsulated cells and allow for ECM deposition as they degrade, demonstrating that synthetic gels can function as 3D cell culture platforms even without integrin-binding ligands. Such inert gels are highly reproducible, allow for facile tuning of mechanical properties, and are simply processed and manufactured.

The gel precursor can be provided to the microfluidic cell culture device, for example to the organoid compartment of a device as described above. After the gel is provided, it is caused to gelate, prior to introduction of a further fluid. Suitable (precursor) gels are well known in the art. By way of example, the gel precursor may be a hydrogel, and is typically an extracellular matrix (ECM) gel. The ECM may for example comprise collagen, fibrinogen, fibronectin, and/or basement membrane extracts such as Matrigel or a synthetic gel. The gel precursor may, by way of example, be introduced into the organoid compartment with a pipette.

The gel or gel precursor may comprise a basement membrane extract, human or animal tissue or cell culture-derived extracellular matrices, animal tissue-derived extracellular matrices, synthetic extracellular matrices, hydrogels, collagen, soft agar, egg white and commercially available products such as Matrigel.

Basement membranes, comprising the basal lamina, are thin extracellular matrices which underlie epithelial cells in vivo and are comprised of extracellular matrices, such a protein and proteoglycans. In one example, the basement membranes are composed of collagen IV, laminin, entactin, heparan sulfide proteoglycans and numerous other minor components (Quaranta et al, Curr. Opin. Cell Biol. 6, 674-681, 1994). These components alone as well as the intact basement membranes are biologically active and promote cell adhesion, migration and, in many cases growth and differentiation. An example of a gel based on basement membranes is termed Matrigel (U.S. Pat. No. 4,829,000). This material is very biologically active in vitro as a substratum for epithelial cells.

Many different suitable gels for use in the method of the invention are commercially available, and include but are not limited to those comprising Matrigel rgf, BME1, BME1rgf, BME2, BME2rgf, BME3 (all Matrigel variants) Collagen I, Collagen IV, mixtures of Collagen I and IV, or mixtures of Collagen I and IV, and Collagen II and Ill), puramatrix, hydrogels, Cell-Tak™, Collagen I, Collagen IV, Matrigel® Matrix, Fibronectin, Gelatin, Laminin, Osteopontin, Poly-Lysine (PDL, PLL), PDL/LM and PLO/LM, PuraMatrix® or Vitronectin. In one preferred embodiment, the matrix components are obtained as the commercially available Corning® MATRIGEL® Matrix (Corning, NY 14831, USA).

The gel or gel-precursor is introduced into the microfluidic device, for example into the well of the organoid compartment of a device described herein and is transported into the microfluidic layer by capillary forces, potentially assisted by gravity. The gel or gel-precursor is confined by a capillary pressure barrier in the microfluidic device, for example to a first sub-volume of the network comprising an organoid compartment and then caused or allowed to gelate.

In one example, the gel or gel-precursor is preloaded with the cell or cells of interest, i.e. the cells are present in the droplet of gel or gel-precursor prior to introduction into the microfluidic cell culture device, for example to an organoid compartment of a device described herein, and prior to gelation. In another example, the cells are inserted into the partially or fully cured droplet after it has been introduced into the microfluidic cell culture device, for example to an organoid compartment of a device described herein. Thus, an alternative culture method comprises seeding the cured droplet of cell culture hydrogel with the cells of interest.

In one example, the gel or gel-precursor is introduced into the microfluidic cell culture device, for example to an organoid compartment of a device described herein, and following gelation, cell mixture, tissue or cell aggregate is placed on top of the gel.

In one example, the at least one type of cell or cell aggregate present in or on top of the droplet of gel or gel-precursor comprises epithelial cells, which during culture can proliferate and/or differentiate depending on the composition of the culture media, other cell types which may be present, and the extracellular matrix. Thus, after introduction into the microfluidic network, either using an aqueous medium, preferably a growth medium, or by using the gel (precursor), the epithelial cells are then allowed to proliferate and/or differentiate in the organoid compartment. Culture of the one or more types of cells or cell aggregates, for example epithelial cells, is achieved by introduction of media into the microfluidic channel and continued under suitable conditions so that the cells are cultured to form an organoid or embryonic body.

In a second example, the at least one type of cell or cell aggregate present in or on top of the droplet of gel or gel-precursor comprises epithelial cells and cells of mesenchymal origin, such as fibroblasts, smooth muscle cells, myofibroblasts, pericytes, astrocytes, oligodendrocytes and the like. Thus, after introduction into the microfluidic network, for example into an organoid compartment, either using an aqueous medium, preferably a growth medium, or by using the gel (precursor), the epithelial cells and the cells of mesenchymal origin are then allowed to interact and form a tissue that can proliferate and/or differentiate in the organoid compartment.

In a further example, the at least one type of cell, for example as a suspension of cells, or cell aggregate present in or on top of the droplet of gel or gel-precursor comprises any combination of epithelial cells and cells of mesenchymal origin, immune cells (such as T-cells, macrophages, Kuppfer cells, dendritic cells, B-cells, granulocytes, mast cells) and/or endothelial cells. For the avoidance of doubt, use of the term "droplet" is not to be construed as meaning that the gel has a typical droplet form or shape. Instead, it is to be construed as meaning the volume of gel that is introduced into and then confined within the cell culture devices described herein.

After the gel is formed, the method comprises introducing or adding a second fluid (second liquid composition) to the microfluidic channel, which will be brought into contact with the gel. In one example, the second fluid is loaded via the well of the organoid compartment. In another example, the second fluid is introduced into the microfluidic channel via a reservoir in fluid communication with the microfluidic channel. In one example, the volume of fluid added is greater than can be contained within the microfluidic channel, resulting in an excess of fluid being retained in the reservoir. The gelled state of the gel droplet ensures that the cells and the gel stay in position, while there is free exchange of metabolites, nutrients and oxygen between the fluid in the microfluidic channel and the organoid compartment.

In the example in which a cell suspension, tissue or cell aggregate is positioned on top of the gel, optionally a second gel volume may be applied to encapsulate the cells, tissue or cell aggregate.

References to cells that "stay in position", are to be understood as being in reference to the initial state as opposed to e.g. being flushed away by viscous drag forces when filling with a second fluid. It goes without saying that a person skilled in the art would recognize that cells in an extracellular matrix environment are still motile through the gel network. Motility is enabled by cell matrix interaction through focal adhesions such as integrins, actin remodelling, by collagenases and many other mechanisms that enable motility of cells in an extracellular matrix environment. Cells might also migrate in and out from the ECM gel during the course of experimentation.

The microfluidic channel further comprises a vent in order to allow for proper filling of the microfluidic channel with expulsion of air from the channel. This vent may be formed either by an additional inlet or by the organoid compartment itself.

It should be noted that typically a flow can be present through the gel, referred to as interstitional flow. Also cells typically have the ability to migrate through and in and out from the gel, due to anchoring points such as integrins. The gel and the fluid accordingly result in an exchange surface without the for need artificial membranes. Within the context of the present Invention, and having the objective to provide a device for cell culture, the first liquid composition will typically comprise a cell culture hydrogel, which, once cured, provides the droplet with a corresponding matrix structure and rigidity. The second fluid typically is an aqueous solution, such as a cell culture medium, a buffer solution, or a test solution, and in certain examples may also include cells as will be described later.

In one example, a droplet of a sufficient volume is introduced such that the cured gel is located substantially entirely within the part of the organoid compartment that is within the microfluidic layer. In one example, the volume of gelled droplet is such that the droplet does not fully block the aperture in the microfluidic cover layer, in which case the unblocked or open region of the aperture can be used as a vent. A vent thus generally comprises an opening or aperture in the cover layer allowing evacuation of air when loading the microfluidic channel through the inlet. In one example, a droplet of a sufficient volume is introduced such that the droplet is confined by the capillary pressure barrier and the majority of the droplet volume is contained within the part of the organoid compartment that is outside of the microfluidic layer, for example wherein the majority of the droplet volume is contained within the well of the organoid compartment.

In a particular embodiment the organoid compartment is flanked at opposite sides with two reservoirs that are in fluid connection by means of first and second inlets to the microfluidic channel. Thus, introduction of a fluid, for example culture media into a first reservoir results in filling of the microfluidic channel. Once filled, a flow of the fluid in the microfluidic channel and reservoirs can be induced. A typical way of doing this is by levelling fluids between the two reservoirs. This is done by having a higher liquid level in one reservoir with respect to the other, or by placing the microfluidic device under an angle. Over time, the two menisci of the fluid (one in each reservoir) will "level", as the system reaches equilibrium with the atmosphere. In order to provide for a continuous flow, periodic re-levelling can be achieved by placing the device on a rocker plate, which periodically adjusts the inclination of the device. In this particular embodiment, the microfluidic channel is typically filled from one inlet and reservoir wherein the second inlet and reservoir functions as a vent during loading the microfluidic channel within the microfluidic network. Alternatively, flow can be induced in the microfluidic channel through use of a pump.

In one example, the fluid introduced into the microfluidic channel may comprise endothelial cells. In general endothelial cells are known as the cells that line the interior surface of the entire circulatory system, from the heart to the smallest lymphatic capillaries. When in contact with blood these cells are called vascular endothelial cells and when in contact with the lymphatic system they are called lymphatic endothelial cells. In a particular embodiment the culture method includes the step of introducing endothelial cells into the microfluidic channel of the microfluidic network, preferably using a second liquid composition, and causing or allowing said endothelial cells to line the microfluidic channel, i.e. causing or allowing the endothelial cells to form a vessel within the microfluidic channel.

Introducing endothelial cells into the microfluidic channel under the right conditions, for example conditions suitable to promote angiogenesis, can result not only in the formation of vascular tissue lining the internal surfaces of the microfluidic channel and in some cases the internal surfaces of the extracellular matrix gel which then becomes permeable, but also outgrowth of new microvessels. The conditions suitable to promote angiogenesis include adding pro-angiogenic compounds such as Fibroblast growth factor (FGF), Vascular Endothelial Growth Factor (VEGF), Angiopoietin-1 (Ang1), Angiopoietin-2 (Ang2), phorbol myristate-13-acetate (PMA), Sphingosine-1-phosphate (S1P), IGFBP-2, hepatocyte growth factor (HGF), prolyl hydroxylase inhibitors (PHi). monocyte chemotactic protein-1 (MCP-1), basic fibroblast growth factor (bFGF) and ephrins amongst others.

When applied as a gradient, the one or more pro-angiogenic compounds can be considered to act as a chemoattractant that promotes directional angiogenesis toward and within the confined gel droplet. In this way, the endothelial cells are stimulated to form a layer of vascular tissue in the microfluidic layer and in the gel which then undergoes permeabilisation and results in outgrowth of new microvessels. The one or more proangiogenic compounds may be added to the droplet of gel or gel-precursor before it is introduced into the organoid compartment, or it may be added to the organoid compartment after formation of the gel droplet. In another example, the one or more proangiogenic compounds may be added to the microfluidic network via another inlet into the microfluidic channel, for example an inlet downstream from the inlet through which the culture media is introduced and/or downstream from the organoid compartment.

In one example, the endothelial cells are introduced into the microfluidic channel after a gel (or gel precursor) optionally loaded with one or more type of cell or cell aggregate to be cultured has been introduced into the organoid compartment. In one example, the endothelial cells are introduced into the microfluidic channel after a gel (or gel precursor) has been introduced into the organoid compartment and subsequently loaded with or covered with one or more type of cell or cell aggregate to be cultured. In other examples, the methods described herein comprise introducing into the organoid compartment a droplet of gel or gel-precursor free from any cell or cell aggregate, allowing or causing gelation, introducing endothelial cells into the microfluidic channel, and then introducing one or more types of cell or cell aggregate to the cured gel or on top of the cured gel. In one example, the endothelial cells are caused or allowed to form a layer of vascular tissue within the microfluidic channel before the one or more types of cell or cell aggregate are introduced into or on top of the gel. In one example, the one or more types of cell or cell aggregate are introduced into the gel by addition of an appropriate amount of gel precursor comprising the cells onto the top of the cured gel.

As already explained herein before, using the capillary pressure barriers enables the formation of stable confined volumes in the organoid compartment so that addition of a second fluid can take place without displacing the gel or its contents. The device of the present invention is thus configured for spatially controlled co-culture with other cells, and provides means to control the composition of the surrounding medium. As such, and within the culture methods of the present invention the fluid loaded into the reservoir (herein also referred to as the second liquid) is any of cell culture media, test solutions, buffers, further hydrogels and the like and may optionally comprise cells or cellular aggregates.

By controlling the composition(s) introduced in the reservoir(s) the cell culture device of the present invention enables different modes of organoid culture. For example, the composition of fluids introduced into the reservoirs can be changed. Such exchange can be a gradient exchange by introducing a new composition in one of the reservoirs and simultaneously removing the fluid from another reservoir within the same microfluidic network till complete exchange has occurred. Such exchange can be discrete, by aspirating fluid from the reservoir and filling it with the new composition. The fluid volume in the reservoir is much larger than the fluid volume in the microfluidic channel and the levelling between reservoirs occurs almost instantaneously, thereby assuring flushing the microfluidic network with the new fluid without the need for emptying the microfluidic channel network during the procedure.

In one example, presence of a second capillary pressure barrier in the device even allows the formation of a layered gel composition. In this example, a first capillary pressure barrier, for example a circular capillary pressure barrier pins a liquid composition comprising a first gel or gel-precursor as a standing droplet on the base layer of the organoid compartment. After this first liquid composition is set, a second gel or gel precursor, optionally containing cells, is loaded in the organoid compartment. This second composition will be retained by a second capillary pressure barrier, for example a circular capillary pressure barrier of larger diameter than the first capillary pressure barrier and concentric with and encircling the first capillary pressure barrier. Through this configuration, the second capillary pressure barrier prevents this second composition from flowing into the microfluidic channel and encapsulates the first gel. The presence of the two capillary pressure barriers accordingly divides the microfluidic network into individual spatial volumes, and gives the user the possibility of spatial configuration in the microfluidic network.

Having the ability to control not only the composition, but equally the fluidic behaviour of the liquid in the microfluidic channel as described previously, the device provides for example the possibility of co-culture with endothelial cells in the microfluidic channel with the formation of a lumen and vascularization of the organoid culture. Luminal perfusion, i.e. vascularization is subsequently possible via one or more reservoirs and the setting in motion of the liquid within said compartments (infra).

Thus, there is also described a method of vascularising one or more cells or cell aggregates, the method generally comprising: introducing into a microfluidic cell culture device a droplet of a gel or gel-precursor and allowing the droplet to be confined by a capillary pressure barrier present in the device; allowing the gel or gel-precursor to cure or gelate to form an at least partially cured gel; introducing a suspension of endothelial cells in a carrier fluid into a microfluidic channel of the microfluidic cell culture device, the microfluidic channel being in fluid communication with the cured gel; allowing the endothelial cells to form at least one microvessel in at least the microfluidic channel; introducing onto a top surface of the cured gel one or more cells or cell aggregates; and allowing or promoting directional angiogenesis between the at least one microvessel and the one or more cells or cell aggregates.

The method is generally performed on a microfluidic cell culture device having a capillary pressure barrier to confine one or more fluids to separate sub-volumes of the device. In one embodiment, the device is such as described herein. However, it will be understood that the method could be performed on other configurations of microfluidic cell culture device and the following description of this method is not to be interpreted as being limited to operation on a device as described herein.

In a first step of the method, the droplet of gel or gel-precursor is introduced into the microfluidic cell culture device, confined by a capillary pressure barrier and allowed to cure or gelate, to form a wholly or at least partially cured gel. References herein to a cured gel are to be understood as meaning a gel which is at least partially cured, as well as being wholly or completely cured. In contrast to the previously described method, the droplet of gel or gel-precursor in this method is free of cells, and comprises any hydrogel known in the art suitable for cell culture, as described above.

Once the droplet of gel or gel-precursor is at least partially, but optionally fully cured, endothelial cells are introduced into a microfluidic channel of the device. Introduction of endothelial cells and conditions for promoting vasculogenesis and/or angiogenesis are described above, and so will not be repeated. The endothelial cells may be introduced as a suspension in a suitable carrier fluid, and allowed or caused to form at least one microvessel in at least the microfluidic channel. In one example, the endothelial cells are caused or allowed to form a layer of vascular tissue within the microfluidic channel before the one or more types of cell or cell aggregate are introduced into or onto a top surface of the at least partially cured gel.

In one example, the microvessel lines the interior walls of the microchannel to an interface with the cured gel, and extends to an inlet and an outlet of the microchannel, thus providing complete vascularisation of the microfluidic channel. In another embodiment, the microvessel extends into the cured gel. Formation of microvessel in the microfluidic channel and optionally also into the cured gel thus provides a vascular bed which can be used to receive biological tissue, for example.

The methods of vascularising one or more cells or described herein comprise introducing one or more cells or cell aggregates, including one or more cell types, into or onto a top surface of the at least partially cured gel. In one example, the one or more cells or cell aggregates, including one or more cell types, are Introduced into or onto a top surface of the at least partially cured gel by addition of an appropriate amount of gel precursor comprising the cells onto the top of the cured gel. In one example, the one or more cells or cell aggregates, including one or more cell types, are introduced into or onto a top surface of the at least partially cured gel, followed by addition of an appropriate amount of gel precursor onto the top surface of the cured gel.

Under the right conditions, directional angiogenesis between the one or more cells or cell aggregates, including one or more cell types, and the microvessel can then take place, leading to vascularisation of the one or more cells or cell aggregates, including one or more cell types, on the microfluidic device. Angiogenesis may be induced or promoted using one or more pro-angiogenic compounds as described previously. The one or more pro-angiogenic compounds may be added onto the at least partially cured gel after the one or more cells or cell aggregates have been introduced.

The one or more cells, or cell aggregates, may comprise one or more epithelial cells and cells of mesenchymal origin, or stromal cells, as described previously. The one or more cells, or cell aggregates may comprise clustered cells, printed cells, an organoid, tissue biopsy, tumor tissue, resected tissue material, organ explant or an embryonic body, depending on the eventual use of the vascularised tissue. The one or more cells, or cell aggregates, may comprise one or more types of cells obtained from, derived from or exhibiting a phenotype associated with a particular biological tissue, for example liver, kidney, brain, breast, lung, skin, pancreas, intestine, retina or hair. The one or more cells or cell aggregates may comprise healthy or diseased tissue, and may be obtained from or derived from a patient.

In one embodiment, the endothelial cells used to vascularise the microfluidic channel and the tissue may also be obtained from or derived from a patient. In one embodiment, the endothelial cells obtained from or derived from a patient may comprise blood outgrowth endothelial cells, or endothelial cells derived from pluripotent stem cells. By using autologous endothelial cells, in combination with a biological tissue comprising one or more cells or cell aggregates from the same patient, the vascularised system is particularly suited to the field of personalised medicine and the development of clinical models and assays to determine or predict the patient's likely response to a particular agent. For example, use of tumor tissue obtained from a patient, along with vascularisation of that tumor tissue using endothelial cells derived from the patient as described above allows for a complete analysis of the patient's likely response to a chemotherapeutic treatment. Furthermore, introduction of one or more types of the patient's own immune cells into such a system allows also for a determination to be made on a likely immune response to a given agent.

The one or more cells, or cell aggregates may undergo a culturing step as described previously, to allow for proliferation and/or differentiation of the cells.

In one embodiment, the one or more cells, or cell aggregates, fully cover the top surface of the at least partially cured gel, thereby forming a barrier layer of tissue on the top surface of the at least partially cured gel. The barrier layer may comprise a monolayer of cells, or a multi-layer of cells or cell aggregates. In one embodiment, the monolayer of cells or the multilayer may be cultured, to allow proliferation and/or differentiation, before or after angiogenesis of the at least one microvessel into the at least partially cured gel. Examples of flat layered tissue include skin tissue (comprising e.g. keratinocytes, adipose tissue and fibroblasts), gut epithelium as well as other epithelial tissues such as lung and retina.

Culture media, or differentiation media may be added to the microfluidic channel as described above, and establishment of a fluid flow through the vascular network may also be achieved as described above, to allow for cell proliferation and/or differentiation. Similarly, compositions of fluids can be controlled as described above. Thus, the vascularised, perfusable network established by the method described allows for the free exchange of metabolites, nutrients and oxygen between the fluid in the microvessel within the microfluidic channel of the device and the cells or cell aggregates on top of the cured gel.

Assay Plate

A further aspect of the present invention provides an assay plate, comprising any of the devices described herein. References to cell culture devices comprising a vascular network and optionally also a biological tissue are to be understood as also referring to an assay plate.

The assay plate may be provided with a gel confined by a capillary pressure barrier in the device. In one particular embodiment, the assay plate may be provided with a gel confined by the capillary pressure barrier to an organoid compartment of the device, wherein the gel or gel-like substance comprises one or more cells or cell aggregates.

The assay plate may comprise one or more cells or cell aggregates which have been cultured by the methods described herein. In one example, at least a part of a microfluidic channel of the device of the assay plate comprises a layer of vascular tissue comprising endothelial cells extending into the gel.

The dimensions of the assay plate may be consistent or compatible with the standard ANSI/SLAS microtitre plate format. In particular the dimensions of the footprint or circumference of the assay plate may be consistent with the ANSI/SLAS standard for microtiter plates.

Also described are assay plates, or cell culture devices produced by any of the methods described herein.

Assays

The assay plate described may be used in an assay, in which a test solution is introduced into the microfluidic network and the effects of the test solution on the cells, cell aggregates or organoid or embryonic body are observed. The test solution may comprise a pharmaceutical drug, a candidate pharmaceutical compound, a toxin, a food compound, a chemical substance, a virus, bacteria, or nanoparticles In one example, the assay plate to be used in the assays comprises a cell culture device comprising a vascularised network, optionally with a biological tissue from a patient. Through the use of autologous endothelial cells, the vascularised system is particularly suited to the field of personalised medicine and the development of clinical assays to determine or predict 35 the patient's likely response to a particular agent. For example, use of tumor tissue obtained from a patient, along with vascularisation of that tumor tissue using endothelial cells derived from the patient as described above allows for a complete analysis of the patient's likely response to a chemotherapeutic treatment. Furthermore, introduction of one or more types of the patient's own immune cells into such a system allows also for a determination to be made on a likely immune response to a given agent.

Suitably, one or more of the patient's own T cells, B cells, lymphocytes, dendritic cells, microglia, and monocytes can be introduced into the assay plate on top of the gel and biological tissue or via a microfluidic channel, along with the test agent. Immune cells may optionally also be present in the gel.

Other uses of the assay plate include in an in vitro cell-based assay, in a pharmaceutical screening assay or in a toxicity assay.

Kits

The present disclosure also provides kits and articles of manufacture for using the cell culture devices and assay plates described herein. In one embodiment, the kit comprises the cell culture devices or assay plates described herein; and one or more pro-angiogenic compounds, for inducing angiogenesis.

The cell culture device or assay plate of the kit preferably comprises a vascular bed, in other words comprises an extracellular matrix gel arranged to receive at least one cell to be vascularised on a top surface thereof; and a vascular network of endothelial cells lining the internal surfaces of the microfluidic channel.

The kit may further comprise a packaging material, and a label or package insert contained within the packaging material providing instructions for inducing angiogenesis in the cell culture device or assay plate using the one or more pro-angiogenic compounds.

The one or more proangiogenic compounds may comprise one or more of Fibroblast growth factor (FGF), Vascular Endothelial Growth Factor (VEGF), Angiopoietin-1 (Ang1), Angiopoietin-2 (Ang2), phorbol myristate-13-acetate (PMA), Sphingosine-1-phosphate (S1P), IGFBP-2, hepatocyte growth factor (HGF), prolyl hydroxylase inhibitors (PHi). monocyte chemotactic protein-1 (MCP-1), basic fibroblast growth factor (bFGF) and ephrins amongst others.

The kits may further include accessory components such as a second container comprising suitable media for introducing the one or more pro-angiogenic compounds, and instructions on using the media.

In related aspects, the present invention provides the use of the cell culture device as described herein for producing and/or culturing cells or tissue, for engineering tissue, for forming embryonic bodies, for forming organoids, and the like.

EXAMPLES

The present invention will now be described by way of example only with reference to the drawings.

Figure 2:
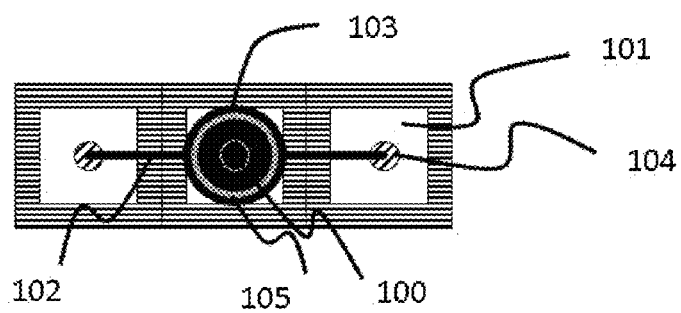
Figure 3:
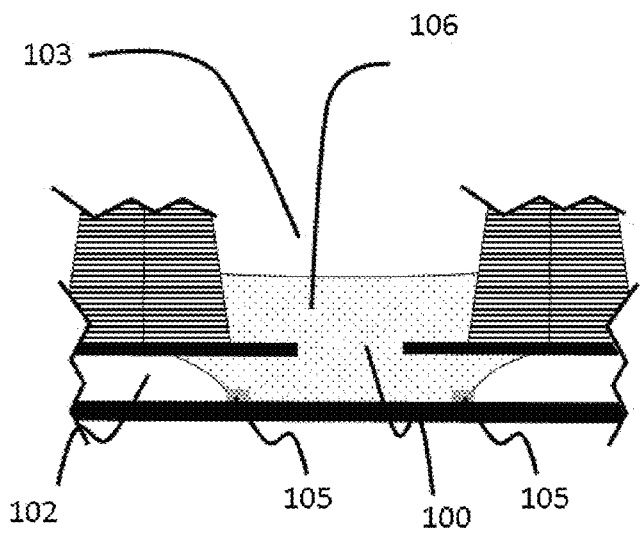

A first example of a cell culture device is schematically shown in FIGS. 1 to 3. The view across the device (FIG. 1) shows a central organoid compartment (103) flanked by two reservoirs (101) and a microfluidic channel (102) in a microfluidic layer (shown in solid) connecting the reservoirs with the organoid compartment via inlets (104) in the cover layer of the microfluidic layer. A capillary pressure barrier (105) is present at the base of the organoid compartment and accessible via aperture (100) in the cover layer of the microfluidic layer (shown in solid). In this particular example, the aperture is of narrower cross-section than the downwardly extending walls of the organoid compartment.

When charged with sufficient volume of the first liquid (the gel or gel precursor (106) (comprising one or more types of cells or cell aggregates, also termed the organoid composition) (106), and having a capillary pressure barrier circumferential to the aperture (100) and with a larger diameter, the former will occlude said aperture (FIG. 3) and so venting of the surrounding microchannel (102) upon addition of a second fluid into one reservoir (101) will occur via microfluidic channel (102) and the inlet (104) of the other reservoir (101).

As shown in the top view (FIG. 2), the circular capillary pressure barrier divides the microfluidic network in two sub-volumes. One sub-volume, in this embodiment the central volume within the capillary pressure barrier, comprises the organoid compartment (103) for receiving the organoid composition, and the second sub-volume defined by reservoirs (101) 35 and microfluidic channel (102) leading to and surrounding the organoid composition in the organoid compartment (103). Microfluidic channel (102) is schematically represented in FIG. 2 as the solid circle surrounding the capillary pressure barrier and the two linear channels extending to reservoirs (101), with the aperture (100) indicated by the dotted line.

The formation of two sub-volumes in direct contact with one another without any intervening structure such as a wall or membrane is one of the key characteristics of the device and assay plate. In addition, through the reservoir and the microfluidic channel it is even possible to control and adapt the medium surrounding the gel, for example the organoid composition. FIG. 3 provides a close up view of the vertical cross section of a part of the microfluidic network, showing the capillary pressure barrier (105) on the base layer and how it confines the droplet of the first liquid (106) (the organoid composition, here depicted without cell or cell aggregates for clarity). The presence of the capillary pressure barrier (105) prevents the gel or gel precursor, for example the organoid composition from filling the microfluidic channels when loaded into the organoid compartment—in other words, in-use the gel or gel precursor is pinned on the capillary pressure barrier (105).

The aperture (100) in FIG. 2 as well in subsequent figures is depicted as a circular shaped aperture. However, it will be understood that the aperture can have any shape, with circular and square being preferred.

Figure 4:
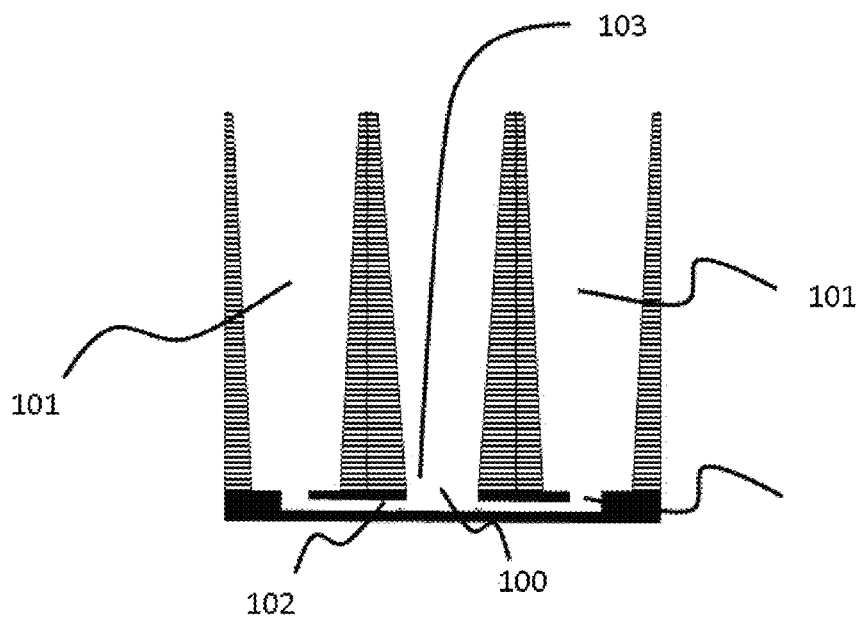
FIGS. 4 to 6 show a vertical cross-section view (FIG. 4), a horizontal top view (FIG. 5), and a close up vertical cross-section view (FIG. 6) of a second possible configuration for a microfluidic network as used in a device according to the present invention.
Figure 5:
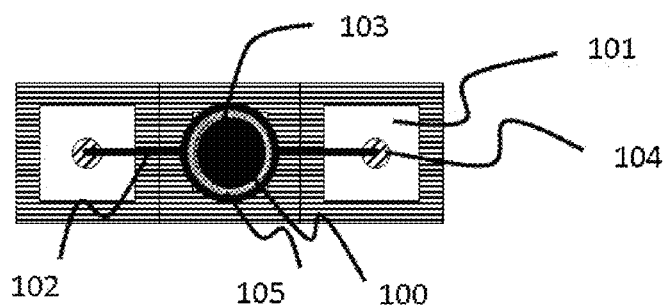
Figure 6:
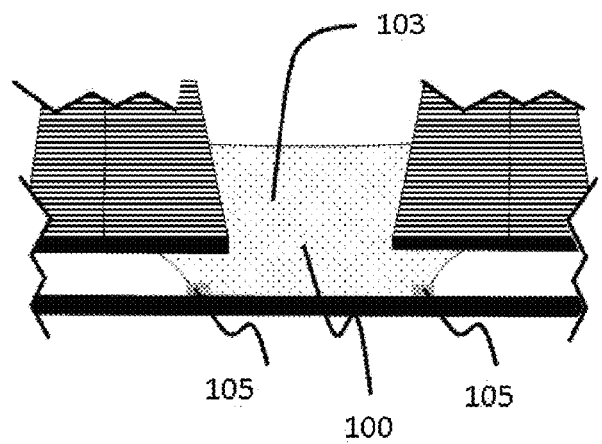

In an alternative embodiment, and as shown in FIGS. 4 to 6, aperture (100) in the cover layer through which organoid compartment (103) extends is enlarged. This enables growing more homogeneous organoids of larger diameter that is not hampered by a sudden restriction of the aperture. Also, it enables a more homogenous distribution of molecules such as growth factors, morphogens, oxygen, nutrients and others throughout the organoid volume through diffusion or interstitial flow. In addition, for the case of vascularisation of the organoid it enables a more homogeneous vascularisation of the organoid volume.

Figure 7:
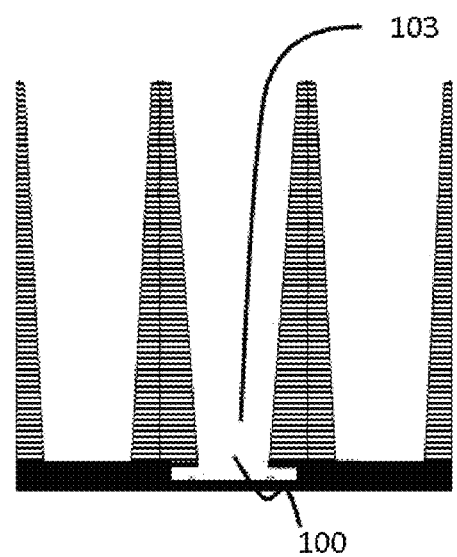
FIGS. 7 to 9 show a vertical cross-section view (FIG. 7), a horizontal top view (FIG. 8), and a close up vertical cross-section view (FIG. 9) of a third possible configuration for a microfluidic network as used in a device according to the present invention.

Being an objective to control the surrounding medium of the organoid composition, additional branches of the microfluidic channel (102) may be present. One such example is provided in FIGS. 7 to 9. In this embodiment a central organoid compartment (103) is connected to four reservoirs (101) in a cross configuration (see FIG. 8), with two linear capillary pressure barriers (105) present, each defining in part the first sub-volume comprising the organoid compartment.

Figure 12:
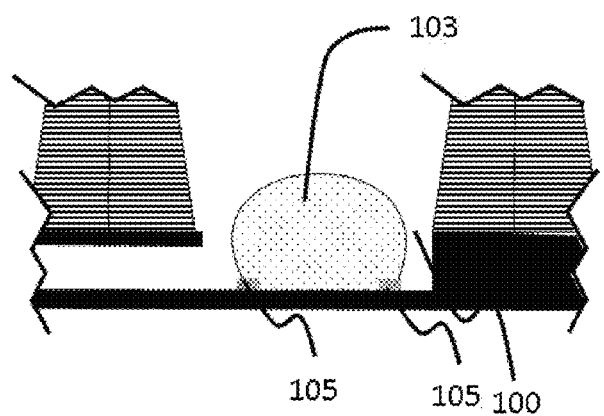

In all of the foregoing examples the capillary pressure barriers are circumferential to the organoid compartment aperture (100) and have larger diameters or areas than the diameter or area defined by the aperture. As such, in all of these examples, loading of the organoid compartment with the gel or gel precursor, for example the organoid composition will result in an occlusion of the aperture. In an alternative embodiment the capillary pressure barrier (105) is positioned within the circumference of aperture (100) (smaller diameter or circumference), such as for example shown in FIG. 12.

With this configuration the gel or gel precursor, for example the organoid composition will be pinned on the barrier as a stable standing droplet. Not only thus, this also results in a larger surface contact area between the two liquids, in addition and different from the foregoing embodiment venting of the surrounding microchannel can occur via the free space between the droplet and the aperture (100) in the cover layer. Thus in one example, the capillary pressure barrier is positioned on the base of the microfluidic channel, but within the circumference of the aperture (the capillary pressure barrier having a smaller diameter).

Figure 14:
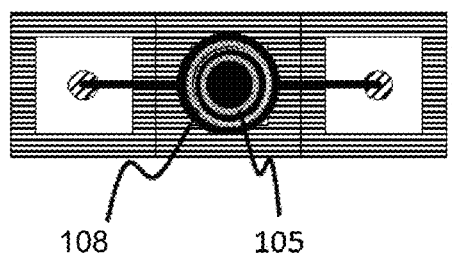
Figure 15:
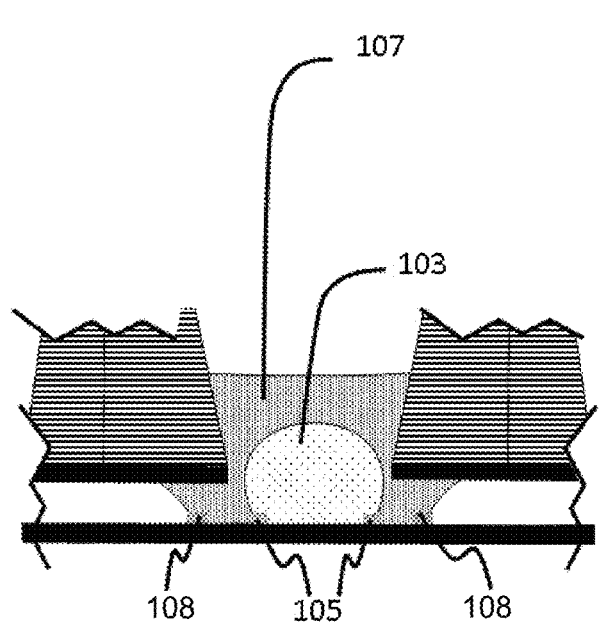

Adding a second capillary pressure barrier of closed geometric configuration even allows for the formation of a layered gel volume composition, for example an organoid volume composition. Such an example is provided in FIGS. 13 to 15. In this example a first circular capillary pressure barrier pins a liquid composition comprising a first gel or gel-precursor as a standing droplet on the base layer of the organoid compartment. After the first liquid composition is set, a second composition (107) is loaded in the organoid compartment. This second composition will be retained by the second capillary pressure barrier (108) thereby preventing this second liquid from filling up the microfluidic channel (102). The presence of the capillary pressure barriers accordingly divides the microfluidic network into individual spatial volumes, and gives the user the possibility of spatial configuration in the microfluidic network.

Figure 16:
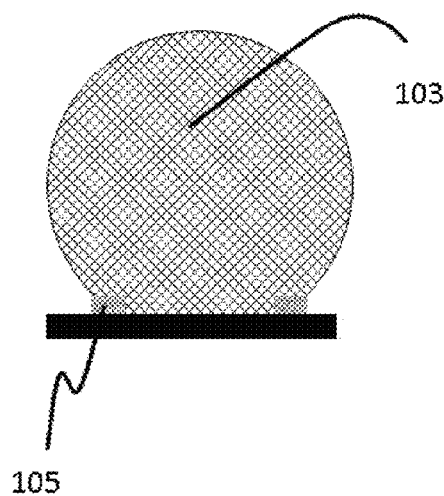
FIGS. 16 to 18 show different forms of capillary pressure barrier as may be used in the microfluidic network in a device according to the present invention.
Figure 17:
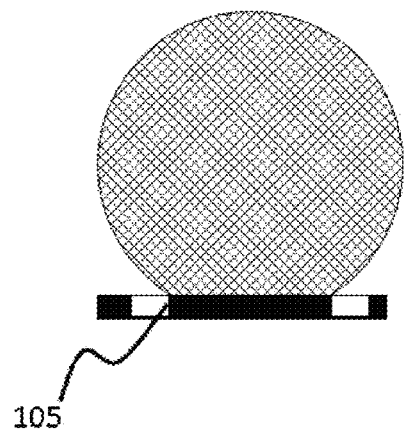
Figure 18:
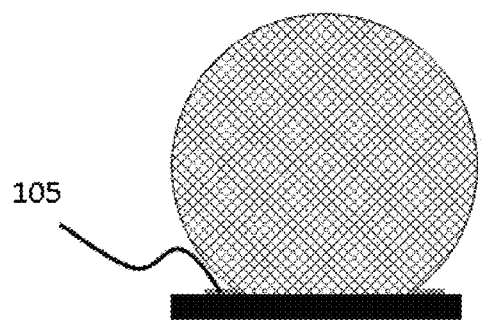

Any capillary pressure barrier used in the device described herein can take different shapes or forms as exemplified in FIGS. 16 to 18, including a protruding rim, a groove or even a line of a hydrophobic material at the base or bottom substrate of the organoid compartment. FIG. 16 shows a capillary pressure barrier constructed as a rim protruding from the bottom substrate which may or may not be constructed of a different material to the bottom substrate or base layer. FIG. 17 provides an example of a capillary pressure barrier constructed as a ridge or groove protruding into the bottom substrate or base layer. FIG. 18 provides an example of a capillary pressure barrier constructed as a line of material of differing hydrophobicity/hydrophilicity. Pinning takes place before the line and that the contact angle of the pinning barrier is described in reference to the horizontal plane of the material of differing hydrophobicity/hydrophilicity.

Figure 13:
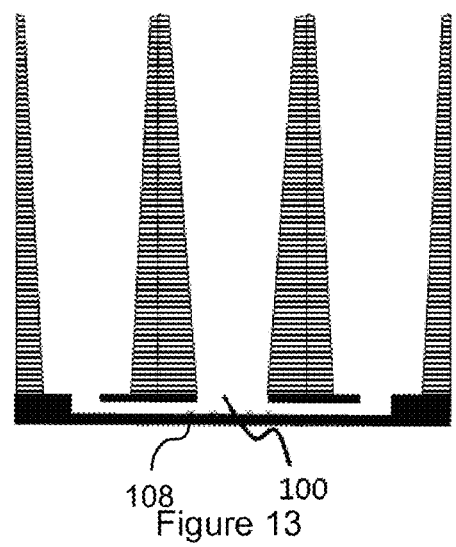
FIGS. 13 to 15 show a vertical cross-section view (FIG. 13), a horizontal top view (FIG. 14), and a close up vertical cross-section view (FIG. 15) of a fifth possible configuration for a microfluidic network as used in a device according to the present invention.
Figure 19:
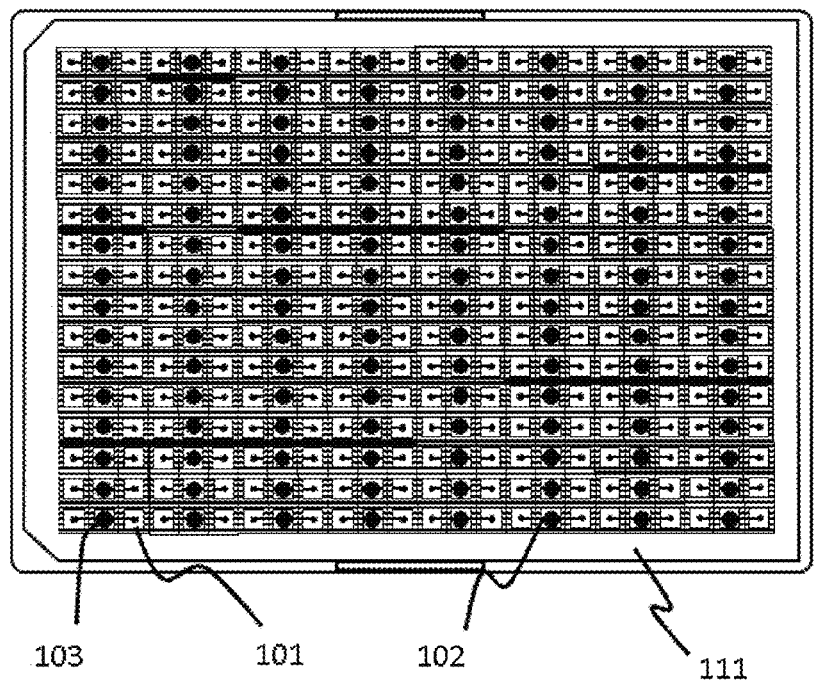
FIGS. 19 and 20 show a bottom view (FIG. 19) and a vertical cross-section view (FIG. 20) of a device according to the invention and consisting of a multi-well configuration of the microfluidic networks as herein described.
Figure 20:
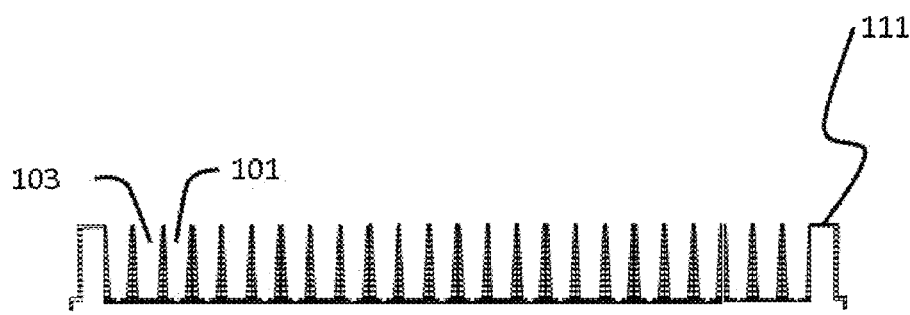

As described, the device is preferably compatible with or based on a microtiter plate footprint as defined by ANSI/SLAS dimensions, as shown in FIG. 19, which shows a bottom view of such a plate comprising 128 separate microfluidic networks such as for example described in FIGS. 1, 4 and 13. FIG. 20 shows a cross-section of the multi-well configuration of FIG. 19, with rim (111) coinciding with the microtitre plate footprint.

Figure 21:
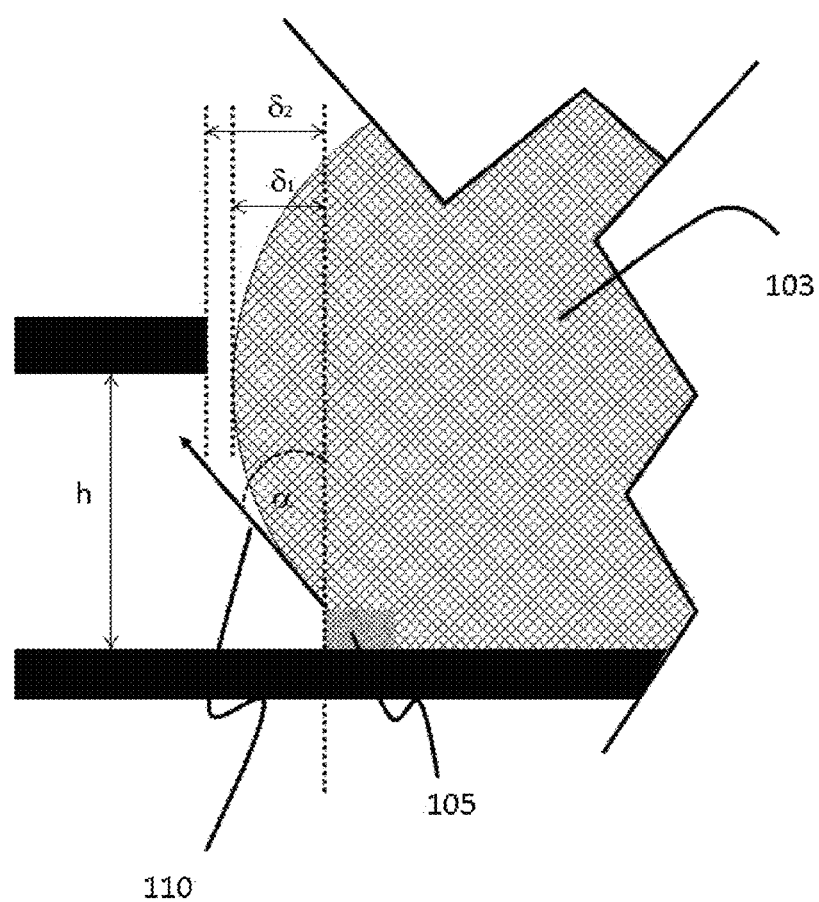
FIG. 21 shows a schematic representation of a device, illustrating an exemplary direction and measure of the liquid-air surface tension on the curvature of a droplet pinned on a capillary pressure barrier.
Figure 22A:
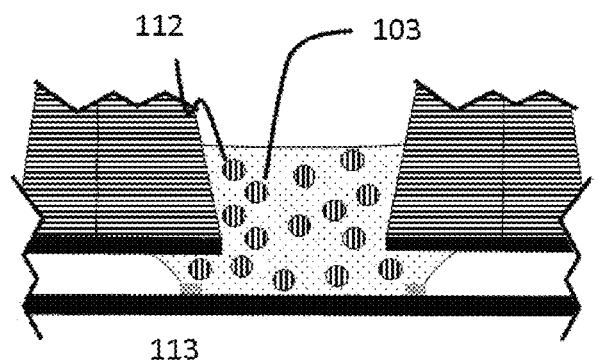
FIG. 22 shows a schematic representation of the steps in a culture method of the present invention.
Figure 22B:
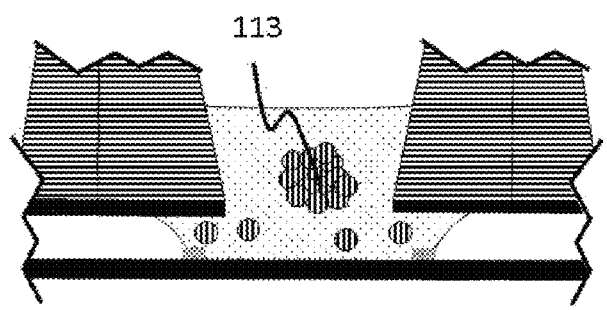
Figure 22C:
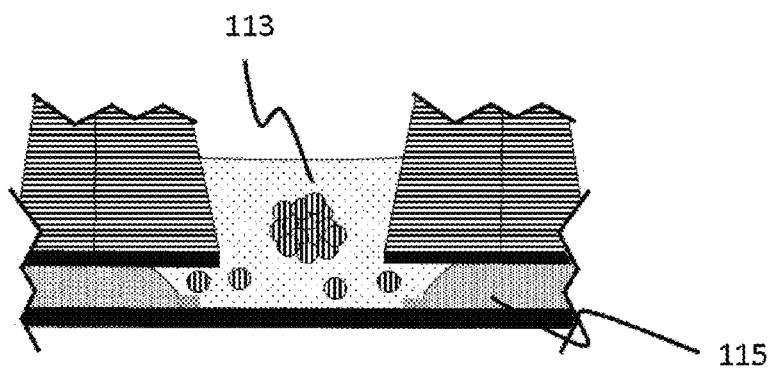
Figure 22D:
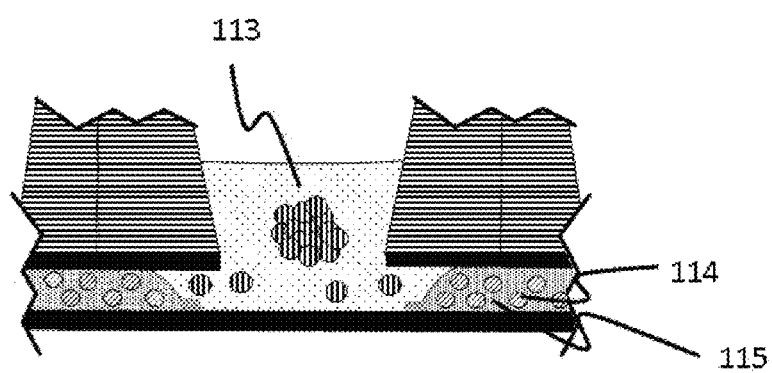
Figure 22E:
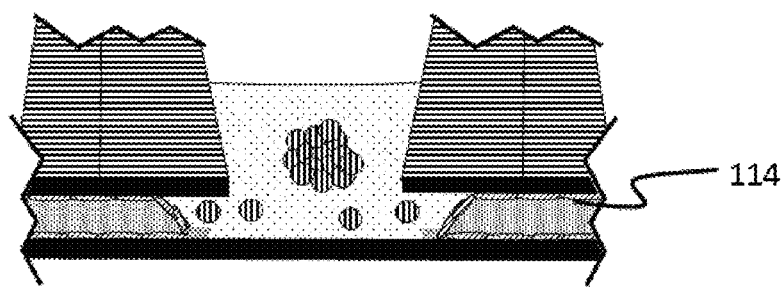
Figure 22F:
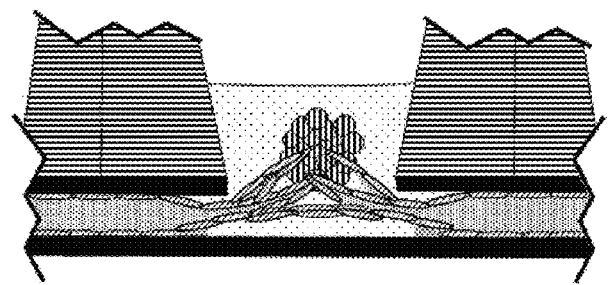

FIG. 21 shows the dimensions to be considered in the case of pinning of the droplet on the droplet retention structures without the droplet touching the cover layer. In this case, the horizontal distance 61 between the exterior of the droplet at the height h of the cover layer and the exterior of the capillary pressure barrier should be smaller than the horizontal distance 62 between the edge of the aperture in the cover layer and the capillary pressure barrier. The curvature of the droplet is determined by the contact angle α with the vertical surface of the capillary pressure barrier, the perimeter of the capillary pressure barrier and the volume of the droplet.

The different steps in using the device described herein to prepare and obtain 3-D culture of cells with the capability of controlling the surrounding medium is shown in FIGS. 22A to 22F. In a first step, a first droplet of liquid comprising cells (112) (FIG. 22A) or cell aggregates (113) (FIG. 22B) is introduced in the organoid compartment (103), pinned on the capillary pressure barrier and allowed to set (cure, gelate). Again, and as already mentioned hereinbefore, the first liquid composition will typically comprise a gel or gel-precursor, for example a cell culture hydrogel (or precursor thereof) and includes any hydrogel known in the art and suitable for the purpose.

Once the droplet of gel comprising the organoid composition is set, the microfluidic channel is loaded with a second liquid (115, FIG. 22C); this is typically an aqueous solution, such as a cell culture medium, a buffer solution, a test solution or an uncured hydrogel. As such, within the device, the interface of the gel comprising the cells and the second liquid in the microfluidic channel results in an exchange surface without artificial boundaries.

Since it is possible to introduce a cell culture medium into the microfluidic channel, it is equally possible to introduce cells into the microfluidic channel. One such embodiment is shown in FIG. 22 D wherein endothelial cells (114) are introduced into the microfluidic channel. These may be introduced as a component of a cell culture or growth media, or may be introduced subsequently. Upon culture of the thus seeded device, and dependent on the composition of the second liquid (the liquid loaded in the microfluidic channel), the endothelial cells (114) may vascularise or line the internal surfaces of the microchannel, i.e. the walls, base and top, and potentially also the ECM gel surfaces (see FIG. 22 E).

In a further step, the culture conditions could allow or induce angiogenesis of the vessels formed in the microfluidic channel (FIG. 22 F), with invasion of the gel droplet comprising the organoid composition and/or capillary vessel formation within the cellular aggregates, organoid or spheroid present therein. Culture conditions allowing angiogenesis are known to the skilled artisan and include for example deprivation of oxygen, mechanical stimulation and chemical stimulation using pro-angiogenic agents such as the pro-angiogenic proteins described previously.

The pro-angiogenic agents could be added to the liquid composition in the microfluidic channel, but equally be added on top of the gel droplet via the organoid compartment. When added on top of the gel droplet present within the organoid compartment, this attracts the endothelial cells into the gel and organoid composition.

A typical spouting mixture comprises VEGF, MCP-1, HGF, bFGF, PMA, S1P in amounts of 37.5 ng/ml to 150 ng/ml for each of VEGF, MCP-1, HGF, bFGF and PMA, and 250 nM to 1000 nM for S1P. An alternative typical sprouting mix composition comprises S1P 500 nM, VEGF 50 ng/ml, FGF 20 ng/ml, PMA 20 ng/ml.

Thus, in a further embodiment, the culture method includes a step of cell culture allowing or inducing angiogenesis of the endothelial cells lining the microfluidic channel walls and gel. In this way, a vessel is formed that connects the inlet and outlet of the microfluidic channel, lines the channel surfaces and extends into the gel comprising an organoid.

Figure 23:
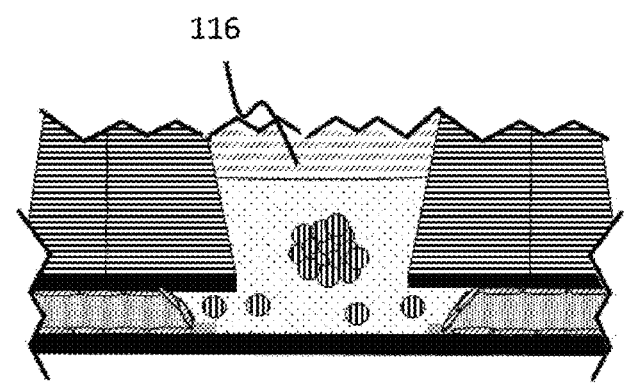
FIG. 23 shows a schematic representation of inducing or allowing angiogenesis to occur and the endothelial cells to invade an organoid composition in a confined droplet.

A chemoattractant or angiogenic agent or composition of different angiogenic agents (116; FIG. 23) to promote angiogenesis can be added onto the gel in the well of the organoid compartment or by another inlet of the microfluidic network that is in contact with a region of the microfluidic channel that communicates with the region of the channel having the lined vessel only through the gel and is thus practically opposite the first region of the channel. The angiogenic compound(s) (or composition) induce(s) the vessel to become permeable, induces sprouting by proliferation and migration in the direction of the gradient. Optionally, once the organoid and organoid gel volume are fully vascularized, a vessel structure can also be formed in a second region of the microfluidic channel.

The preferable result of this method is an organoid in a gel that is vascularized by microvessels that connect to a larger vessel via one or more microfluidic channels through which a flow of growth medium, serum or other can be applied. As such, and using the device, it is possible to co-culture a first type of cells in a first confined sub-volume of the network comprising the organoid compartment with culture of endothelial cells in the second sub-volume comprising the microfluidic channel, to achieve a vascularized model of the cellular aggregates, organoid or spheroid present within the gel droplet of the organoid composition, which is connected to the reservoir(s) by means of the endothelial vessels formed within the microfluidic channels.

The vessel formed by vascularisation of the microfluidic channel has a lumen that is the apical side of the vessel, while the outside of the vessel is the basal side. In one example, the pro-angiogenic compounds or composition thereof is/are applied on the basal side of the vessel in order to induce directional angiogenesis.

Thus, and differently to existing models, the use of the device allows the induction of a flow of medium across a vascularized model of the cellular aggregates, organoid or spheroid present within the gel droplet of the organoid composition.

Figure 24:
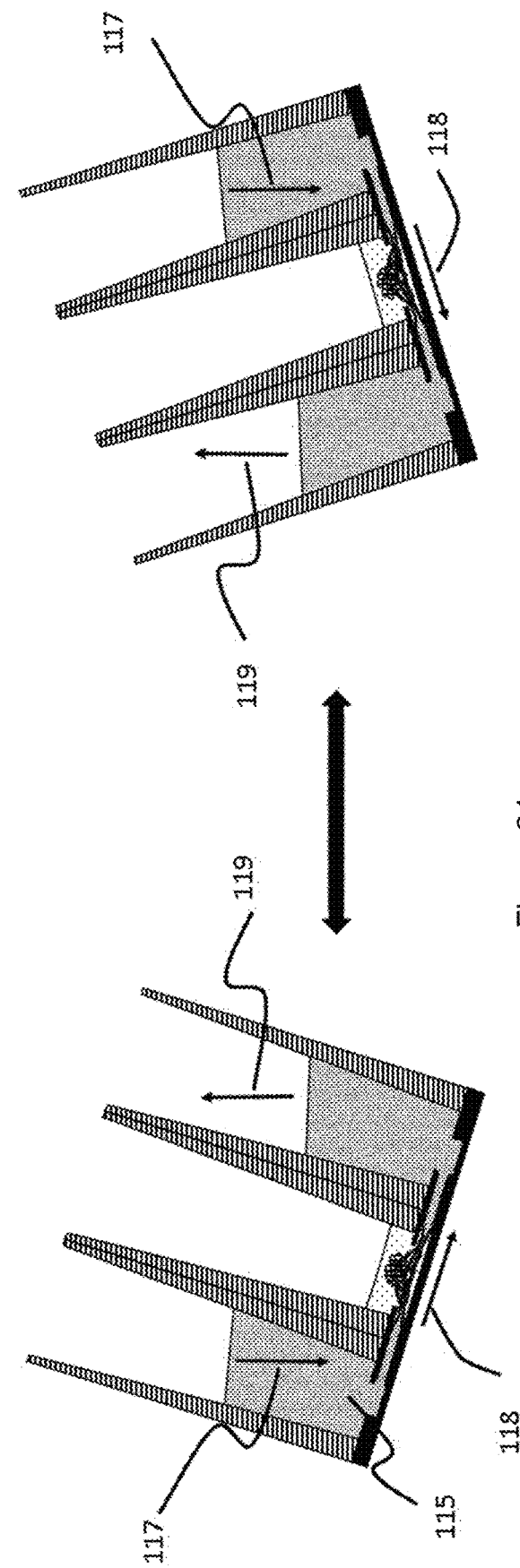
FIG. 24 shows a schematic representation of a method for inducing a flow through the vascularized organoid composition by levelling of media between an upstream and a downstream reservoir of the device.

Culture method steps in which the liquid in the reservoir is set in motion; as well as methods including steps in which the liquid in the microfluidic channel is set in motion, are within the ambit of the methods. A simple example is provided in FIG. 24 showing a rocking movement of the microfluidic network, i.e. whereby placing the device under an inclination angle induces a flow and whereby flow is maintained by periodically changing the inclination angle, with respective rise (119) and fall (117) of the liquid level in the reservoirs communicating (118) via the microfluidic channels and vascularized organoid compartment.

Figure 25:
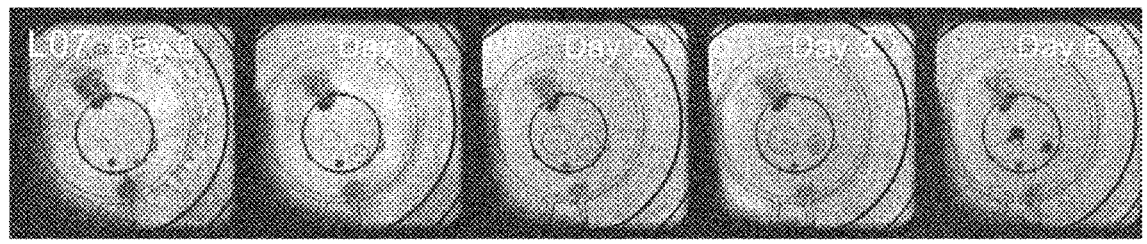
FIG. 25 shows a high resolution image looking down through an organoid compartment of a cell culture device showing organoid growth within an extracellular matrix gel confined to an organoid compartment by a capillary pressure barrier.

FIG. 25 shows the experimental result of culturing intestinal (gut) organoids in a Matrigel ECM confined by a capillary pressure barrier, with a flow of growth medium introduced via a microfluidic channel. Between days 3 and 6, the growth medium was not changed, resulting in cell death.

Figure 8:
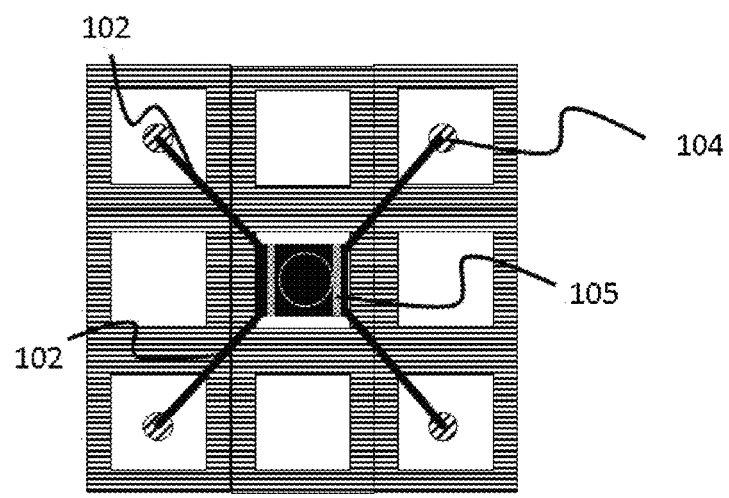
Figure 9:
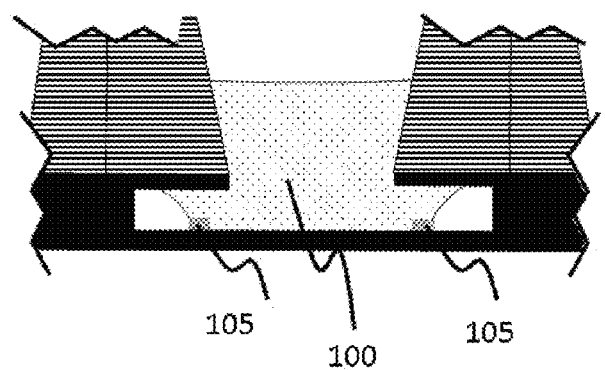
Figure 10:
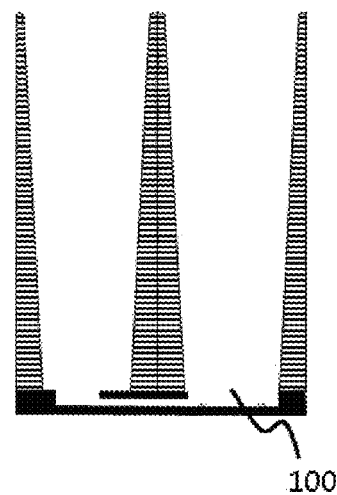
FIGS. 10 to 12 show a vertical cross-section view (FIG. 10), a horizontal top view (FIG. 8), and a close up vertical cross-section view (FIG. 9) of a fourth possible configuration for a microfluidic network as used in a device according to the present invention.
Figure 11:
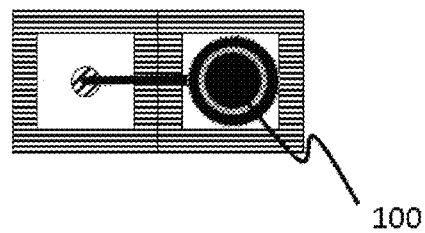
Figure 26:
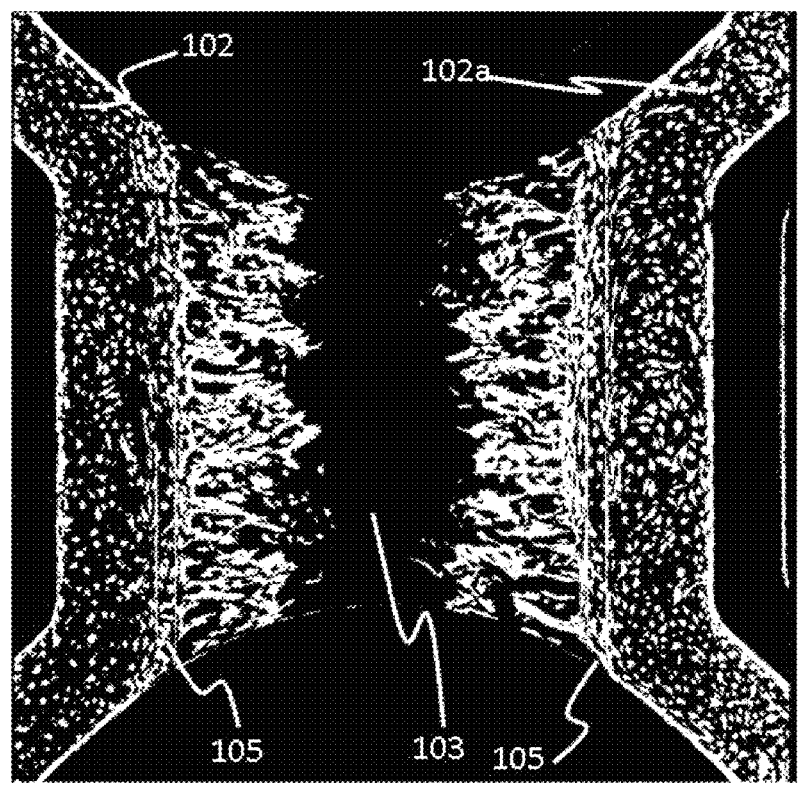
FIG. 26 shows a high resolution image looking down through an organoid compartment of a cell culture device showing angiogenesis within an extracellular matrix gel confined to the organoid compartment of the apparatus of FIG. 8.
Figure 27A:
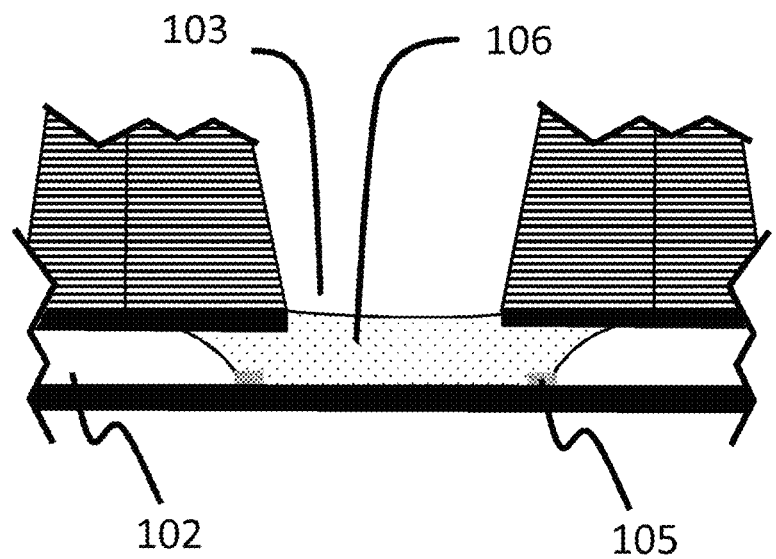
FIGS. 27 A to E show a schematic representation of the steps in a culture method of the present invention.
Figure 27B:
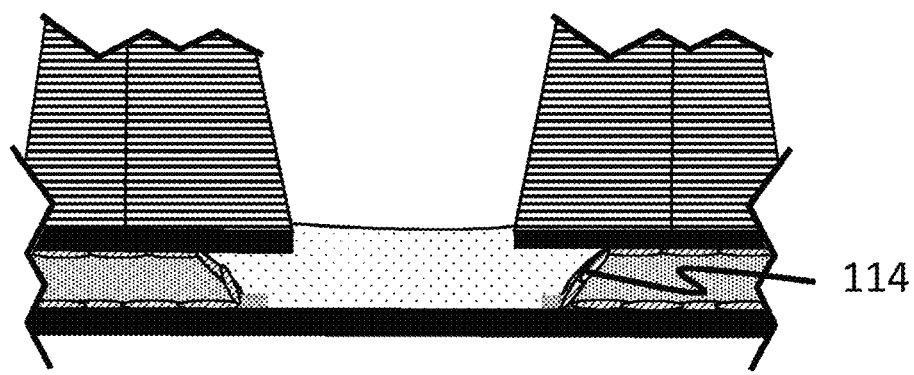
Figure 27C:
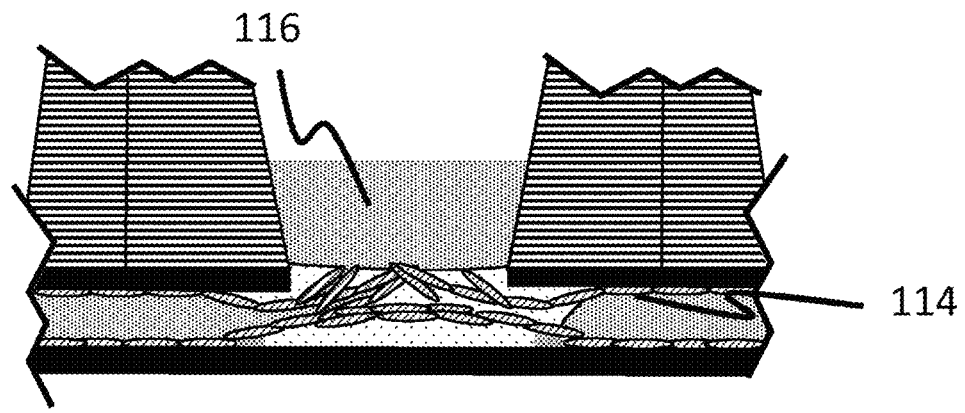
Figure 27D:
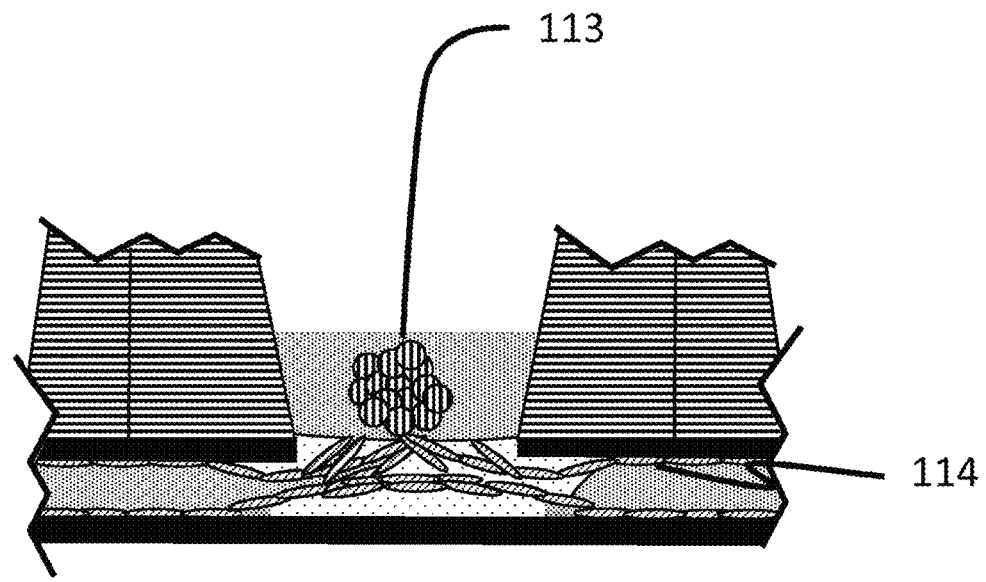
Figure 27E:
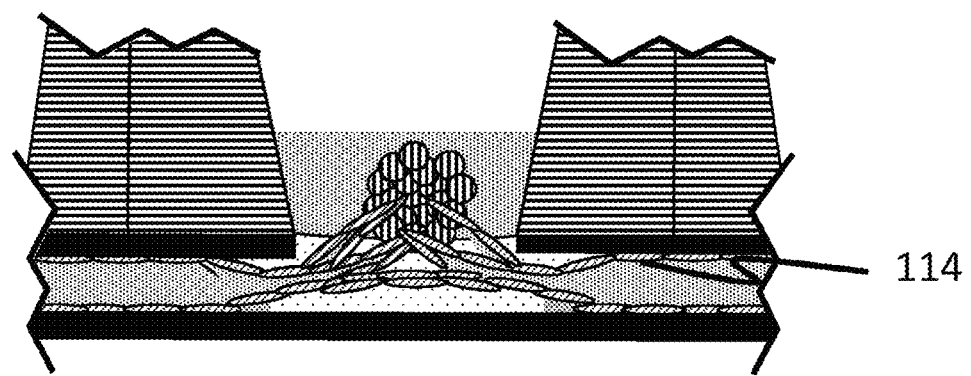

FIG. 26 shows the experimental result of inducing angiogenesis in a cell culture device according to FIG. 8. A gel droplet was introduced into the organoid compartment (103), pinned by the linear capillary pressure barriers (105) and allowed to gelate. Once gelled, endothelial cells (HUVECs) were introduced into microfluidic channels 102/102a. The endothelial cells were allowed to form a vessel within the microfluidic channels, thereby lining the channel walls and gel. Subsequently, a composition of pro-angiogenic compounds (VEGF, FGF, PMA and S1P) was added on top of the gel, stimulating angiogenesis within the gel, as evidenced by the formation of microvessels within the organoid compartment. For the avoidance of doubt, this particular experiment was carried out in the absence of any organoid or spheroid within or on top of the gel, so that the vascularisation within the gel can be seen.

The steps of the method for vascularising a cell aggregate is shown in FIGS. 27 A to 27 E. While this particular embodiment demonstrates the method as being carried out on a particular configuration of microfluidic cell culture device, it will be understood that the method is more generally applicable to other configurations of microfluidic cell culture device. In a first step, a droplet of a gel or gel precursor, free of cells or cell aggregates, (106) (FIG. 27A) is introduced into the organoid compartment (103), pinned on the capillary pressure barrier (105) and allowed to set (cure, gelate).

Once the droplet of gel is set, the microfluidic channel (102) can be loaded with a second liquid, typically an aqueous solution, such as a cell culture medium, a buffer solution, a test solution or an uncured hydrogel. As such, within the device, the interface of the gel and the 20 second liquid in the microfluidic channel results in an exchange surface without artificial boundaries.

Since it is possible to introduce a cell culture medium into the microfluidic channel, it is equally possible to introduce cells into the microfluidic channel. One such embodiment is shown in FIG. 27 B wherein endothelial cells (114) are introduced into the microfluidic channel. These may be introduced as a component of a cell culture or growth media, or may be introduced subsequently. Upon culture of the thus seeded device, and dependent on the composition of the second liquid (the liquid loaded in the microfluidic channel), the endothelial cells (114) may vascularise or line the internal surfaces of the microchannel, i.e. the walls, base and top, and potentially also the ECM gel surfaces (see FIG. 27 B).

In a further step, the culture conditions could allow or induce angiogenesis of the vessels formed in the microfluidic channel (FIG. 27 C), with capillary vessel formation within the gel droplet. Culture conditions allowing angiogenesis are known to the skilled artisan and include for example deprivation of oxygen, mechanical stimulation and chemical stimulation using pro-angiogenic agents such as the pro-angiogenic proteins described previously.

The pro-angiogenic agents could be added to the liquid composition in the microfluidic channel, but equally be added on top of the gel droplet via the organoid compartment. When added on top of the gel droplet present within the organoid compartment, this attracts the endothelial cells into the gel.

Thus, in a further embodiment, the method includes a step of cell culture allowing or inducing angiogenesis of the endothelial cells lining the microfluidic channel walls and gel. In this way, a vessel is formed that connects the inlet and outlet of the microfluidic channel, lines the channel surfaces and extends into the gel.

A chemoattractant or angiogenic agent or composition of different angiogenic agents (116; FIG. 27 C) to promote angiogenesis can therefore be added onto the gel. The angiogenic compound(s) (or composition) induce(s) the vessel to become permeable, induces sprouting by proliferation and migration in the direction of the gradient.

Following angiogenesis into at least a part of the gel, a cell aggregate (113) may be introduced onto the top surface of the gel (FIG. 27 D). This step may be realised by introducing the cells in a suitable carrier liquid, such as buffer or growth media, such that the cells are submerged below the air-liquid interface of the carrier liquid, as shown in FIG. 27 D. Alternatively, and particularly in the example of a cell aggregate such as an organoid or a tissue explant, this step may be realised in the absence of any carrier liquid, using techniques for manipulating and transporting cells that are known in the art, such as microsuction techniques.

Finally, through the use of one or more proangiogenic compounds as described above, and/or through the nature of the cells of the cell aggregates (113) themselves, angiogenesis between the endothelial cells (114) forming the microvessel and the cell aggregates (113) can be allowed or induced (FIG. 27 E), resulting in the respective sprouting blood vessels joining to form a fully vascularised system.

Figure 28:
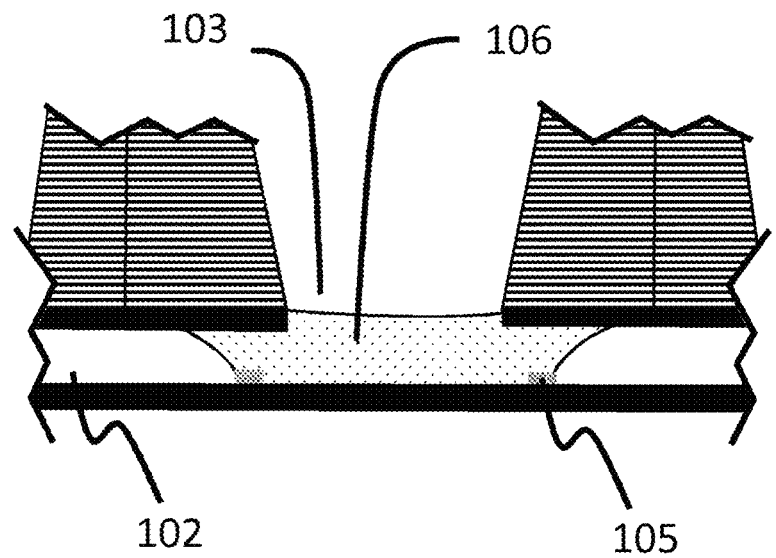
FIGS. 28 A to 28 D show an alternative method to that described in FIGS. 27A to 27E.
Figure 28:
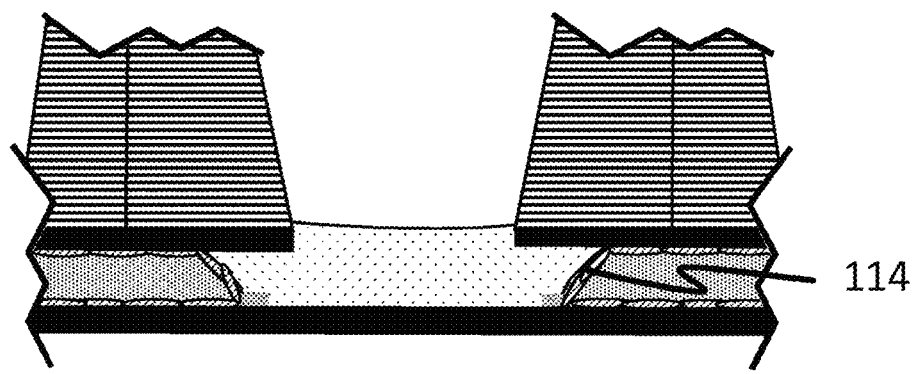
Figure 28:
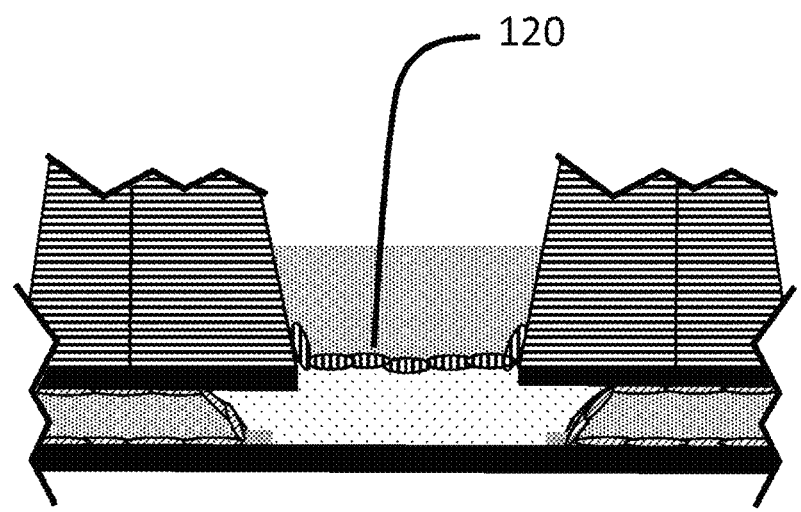
Figure 28:
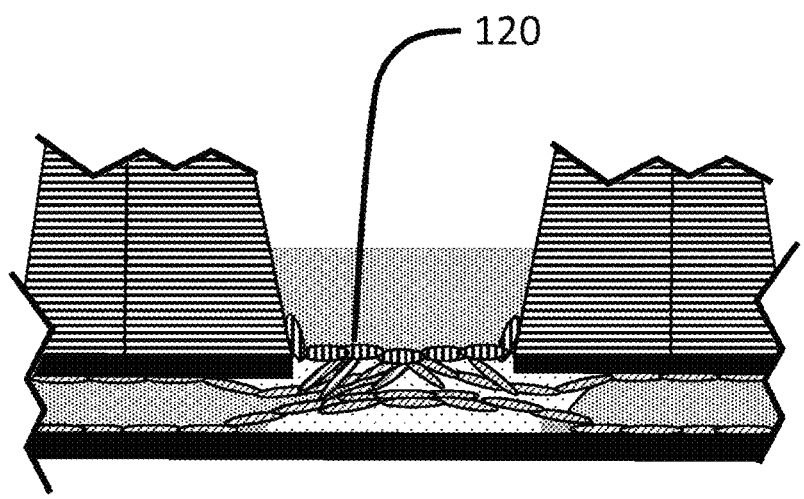

An alternative method to that illustrated in FIG. 27 is shown in FIGS. 28 A to 28 D. The steps of FIGS. 28 A and 28 B correspond to those of FIGS. 27 A and 27B, so will not be discussed further. Following vascularisation of the microchannel (102), but before angiogenesis of the microvessel into the gel, a monolayer of cells (120) is added on top of the gel, covering its entire top surface (FIG. 28 C). While this is depicted as a true monolayer, it will be understood that this could also result in deposition of multiple layers of cells, in particular a tissue of multiple layers, optionally of different cell types. For example, a skin tissue sample, a mixture of different skin cell types, or a sample of stem cells which can subsequently differentiate into different types of skin cells can be introduced.

Angiogenesis of the microvessel into the gel and to the layer of cells covering the top surface of the gel can then be induced or promoted as described previously (FIG. 28 D).

As with the method of FIG. 22, the result of both of the methods shown in FIGS. 27 and 28 is biological tissue formed of one or more cells or cell aggregates, for example an organoid, on the top surface of a gel, that is vascularized by microvessels that connect to a larger vessel via one or more microfluidic channels through which a flow of growth medium, serum or other can be applied. As such, and using the device, it is possible to co-culture a first type of cells in a first confined sub-volume of the network comprising the organoid compartment with culture of endothelial cells in the second sub-volume comprising the microfluidic channel, to achieve a vascularized model of the cellular aggregates, organoid or spheroid present on a top surface of the gel droplet, which is connected to the reservoir(s) by means of the endothelial vessels formed within the microfluidic channels.

Thus, and differently to existing models, the use of the device allows the induction of a flow of medium across a vascularized model of the cellular aggregates, organoid or spheroid present on a top surface of the gel droplet.

Figure 29:
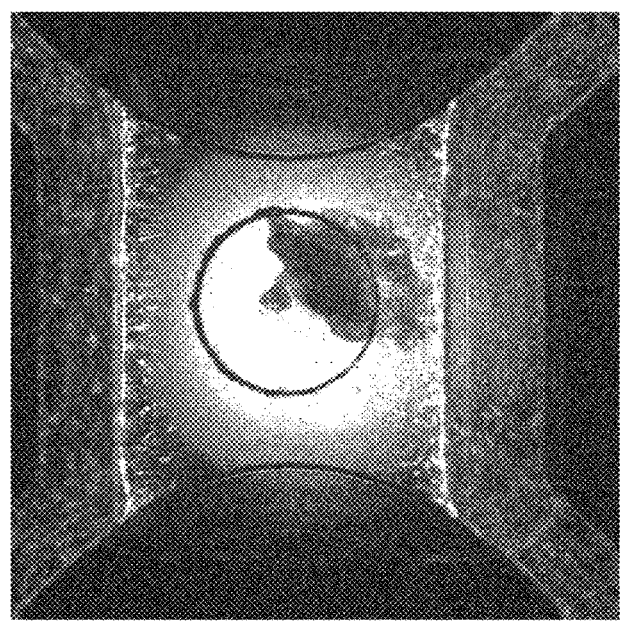
FIG. 29 shows a high resolution image of a kidney organoid that is placed on a vascular bed at the day of transplanting the organoid onto the bed.

FIG. 29 shows a high resolution image of a kidney organoid that is placed on a vascular bed on the day of transplantation of the organoid onto the bed. In this image, viewed from above, the white lines running from top to bottom are the locations of the capillary pressure barriers, representing the boundary between an extracellular matrix gel and two vascularized microchannels, one on each side. As can be seen, vasculature from the microchannels has already started sprouting into the extracellular matrix gel.

Figure 30:
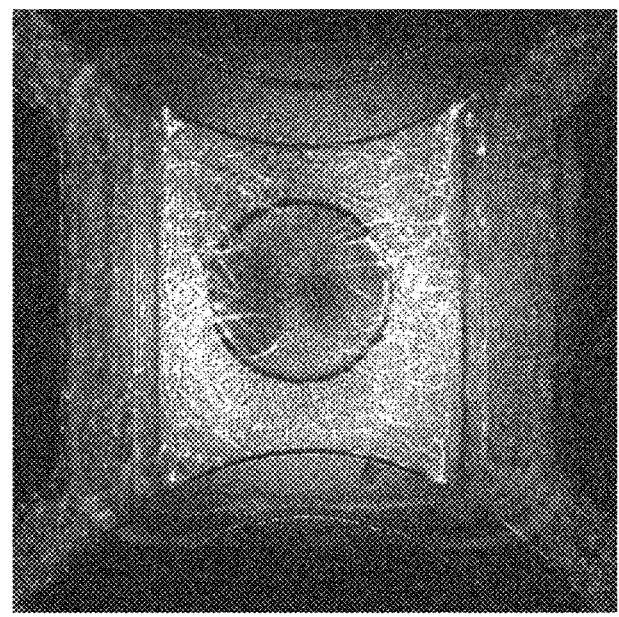
FIG. 30 shows a high resolution image of a kidney organoid 7 days after transplantation of the organoid onto a vascular bed.

FIG. 30 shows a high resolution image of a kidney organoid 7 days after transplantation of the organoid onto a vascular bed. As can be seen in this image, after 7 days, extensive angiogenesis into the extracellular matrix gel has occurred, along with outgrowth of vasculature from the organoid, to the extent that the organoid is now part of a vascular network extending into the microchannels.

Figure 31:
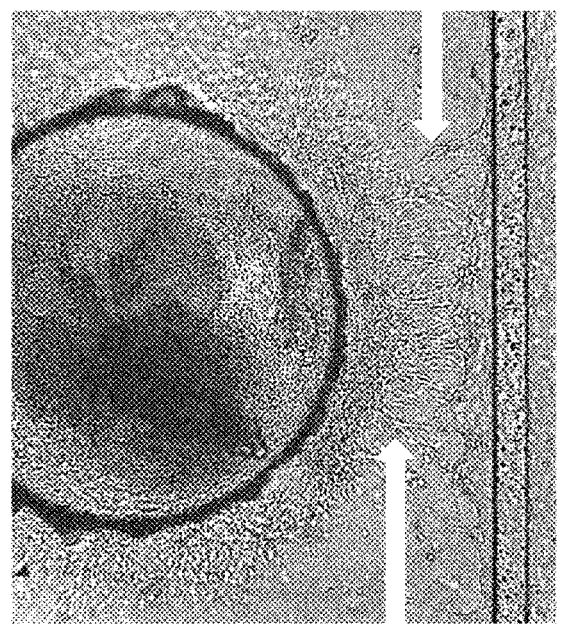
FIG. 31 shows a high resolution image of a mouse embryonic kidney explant 7 days after transplantation of the kidney explant onto a vascular bed.

FIG. 31 shows a high resolution image of a mouse embryonic kidney explant 7 days after transplantation of the organoid onto a vascular bed. The dark lines running top to bottom on the right hand side of the image are a capillary pressure barrier, with a microchannel to the right and an organoid compartment (containing the kidney explant) to the left. The white arrows show the human umbilical vein endothelial cells (HUVEC) vessels connecting with the outgrown vasculature of the embryonic mouse kidney.

Figure 32:
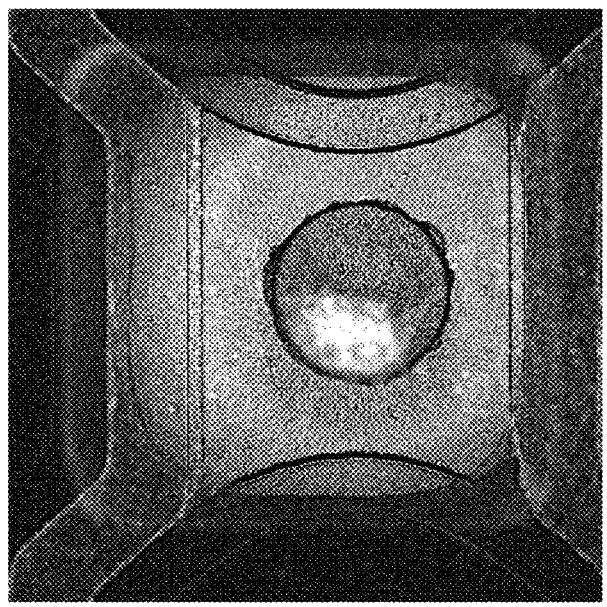
FIG. 32 shows a high resolution image of a liver spheroid consisting of hepatocytes and RFP-labeled HUVECs at day 7 after transplantation onto the vascular bed.

FIG. 32 shows a high resolution image of a liver spheroid consisting of hepatocytes and RFP-labeled HUVECs at day 7 after transplantation onto the vascular bed; The endothelium of the liver spheroid connects with the vascular bed. The picture shows phase contrast and red fluorescence.

Figure 33:
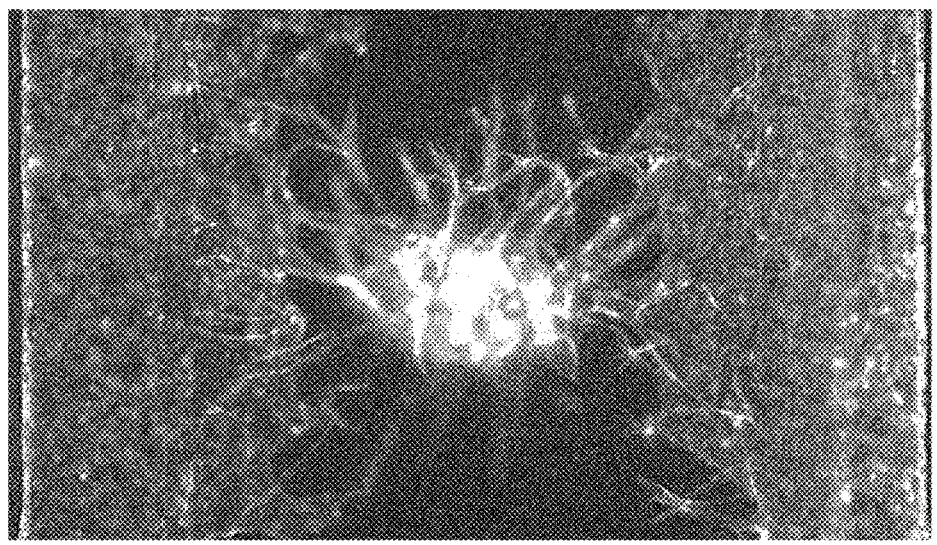
FIG. 33 shows a high resolution image of the same system as shown in FIG. 32, showing red fluorescence of the endothelium.
Figure 34:
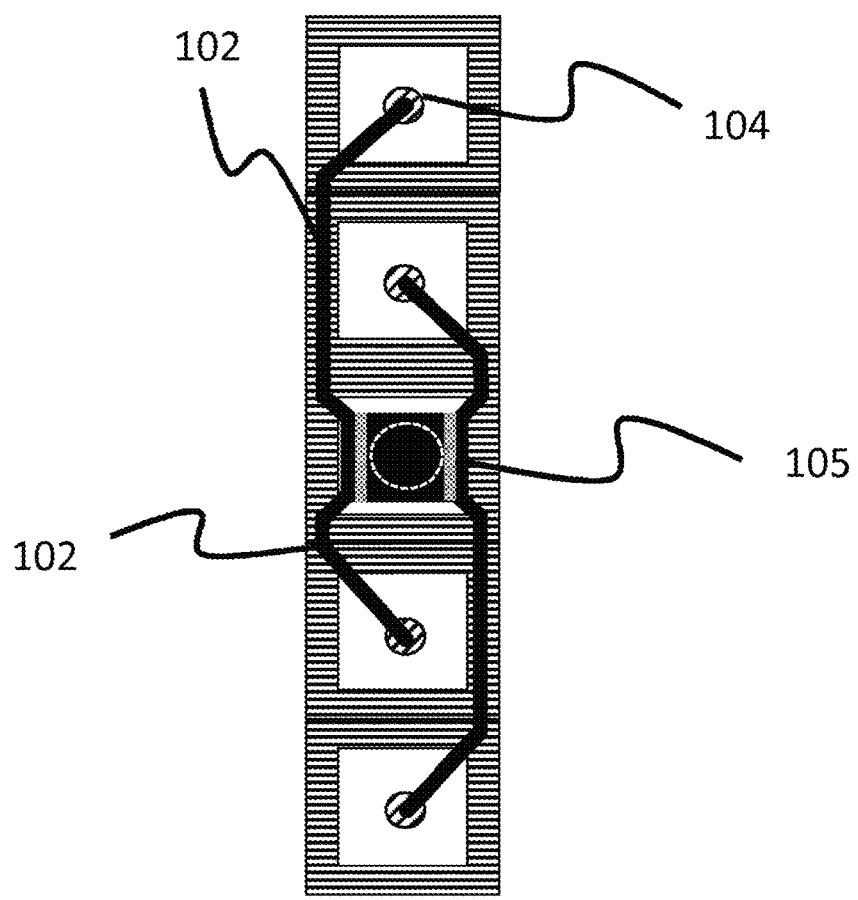
FIG. 34 shows a horizontal top of an alternative possible configuration for a microfluidic network as used in a device according to the present invention.

FIG. 33 shows a high resolution image of the same system as shown in FIG. 32, showing red fluorescence of the endothelium; and FIG. 34 shows a horizontal top of an alternative possible configuration for a microfluidic network as used in a device according to the present invention. The configuration is a modification of FIG. 8, in which the channels and inlets are chosen such that all inlets are in one single row. This configuration is particularly advantageous over other configurations as each network takes up less space on the device.

Figure 35:
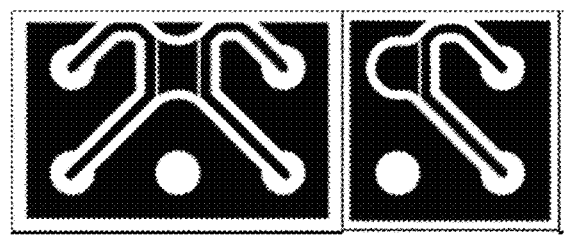
FIG. 35 shows two more possible configurations of microfluidic networks as used in a device according to the present invention.

FIG. 35 shows a horizontal top view of two alternative possible configurations for a microfluidic network as used in a device according to the present invention. Each configuration is particularly advantageous when multiple networks of each type are used in a 96 well plate format as all of the respective microchannel inlets of the networks are placed in-line at a pitch of a 8-multi pipette pitch, as are all of the respective gel inlets and all of the respective microchannel outlets. This allows use of multi-channel pipetting (for example by a robot) to simultaneously fill multiple networks in one action.

Example Protocols

A series of exemplary protocols for performing the methods of the present invention will now be described. It will be understood that these are by way of example only and that different reagents or conditions may also be used.

Gel Preparation to Create a Scaffold for Vasculature

To suppress premature polymerization of collagen, gel preparation steps are carried out on ice. In this method, the gel is composed of 4 mg/mL Collagen I (AMSbio Cultrex 3D Collagen I Rat Tail, 5 mg/mL, Cat. 3447-020-01), 100 mM HEPES (Life Technologies, 15630-122) and 3.7 mg/mL $NaHCO_3$ (Sigma, Cat. S5761-500G). The collagen was mixed with the HEPES and the $NaHCO_3$ and was dispensed in the gel inlet of the organoid compartment of a microfluidic network according to FIG. 8 and incubated at 37° C. for at least 20 minutes. The gel volume will depends on the application, but as little as 1 µL of collagen gel can be dispensed into the device—in this method it will create a cup-like shape (i.e. with a concave top surface) which will later aid in positioning of an organoid, a tissue, or an aggregate of cells.

Seeding Endothelial Cells into the Microchannel

After gelation, endothelial cells (e.g. HUVECs or any other endothelial cell source), as a suspension of single cells in suitable medium (for example Endothelial Cell Growth Medium MV2 from PromoCell) are dispensed into the microchannel inlet of one or both microchannels. Suitably, 2 µL of endothelial cells should be dispensed to each microchannel at the concentration of at least $0.5 \times 10^6$/mL. When it is desired that both microchannels are vascularised, there are two main methods of seeding:

1. Sequential seeding, in this method 2 µL of endothelial cells are dispensed at the concentration of at least 0.5×10E6/ml in the first microchannel. The plate is positioned on its side in the incubator at 37° C. for at least 15 minutes to aid endothelial cell adhesion to the gel. After this period, an additional 20 µL of medium is dispensed to the same inlet to avoid evaporation inside of the channel. Next, seeding of the second microchannel is performed. Another 2 µL of endothelial cell suspension is dispensed at a concentration of at least $0.5 \times 10^6$/mL into the second microchannel. The plate is positioned on its side for at least 15 minutes to aid endothelial cell adhesion to the gel. After this period, an additional 20 µL of medium is dispensed to the same inlet to avoid evaporation inside of the channel. The plate is incubated at 37° C. for at least 1 hour under stationary conditions. Next, an additional 30 µL of medium is added to each of the microchannel inlets and 50 µL of medium is dispensed to each of the microchannel outlets. The plate is placed on a rocking platform, at maximum inclinations of 7°, with 8 minute intervals.

2. Simultaneous seeding: in this method 2 µL of endothelial cells are dispensed at a concentration of at least $1 \times 10^6$/mL to each inlet of both microchannels. The plate is held stationary at 37° C. in the incubator. After 15 minutes, an additional 20 µL of medium is added to each of the two inlets and the plate is incubated at 37° C. for at least 1 h. Next, an additional 30 µL of medium is added to each of the microchannel inlets and 50 µL of medium is dispensed to each of the microchannel outlets. The plate is placed on a rocking platform, at maximum inclinations of 7°, with 8 minute intervals.

In an alternative method of simultaneous seeding, 2 µL of endothelial cells are dispensed at a concentration of at least $1 \times 10^6$/mL to each of the inlets of both microchannels. The plate is positioned on a 180° rotator device (3 rotation per minute) at 37° C. in the incubator. After 15 minutes, an additional 20 µL of medium is added to each inlet and the plate is incubated on the 180° rotator device at 37° C. for at least 1 h. Next, an additional 30 µL of medium is added to the each of the microchannel inlets and 50 µL of medium is dispensed to each of the microchannel outlets. The plate is placed on a rocking platform, at maximum inclinations of 7°, with 8 minute intervals.

Depending on the endothelial cells' behaviour, vessels are cultured for 1 or 2 or 3 or more days before angiogenesis is induced, or any organoid/tissue/cell aggregate are placed onto the gel. During this process, a proangiogenic composition can be added, to create a gradient of angiogenic factors which stimulate sprout formations towards the source of the factor.

For example, proangiogenic factors such as Vascular endothelial growth factor (VEGF), Monocyte chemotactic protein-1 (MCP-1), Hepatocyte growth factor (HGF), Basic fibroblast growth factor (bFGF), Phorbol myristate acetate (PMA), Sphingosine-1-phosphate (S1P) can be used for sprout formation, separately or in combination.

In this method at least 20 µL, for example up to 50 µL, of proangiogenic factor cocktail (for example VEGF 50 ng/ml, bFGF 20 ng/ml, S1P 500 nM, PMA 20 ng/ml) in an endothelial medium (for example MV2) can be dispensed to the gel inlet to induce sprout formation. Vessels are induced with the angiogenic factor cocktail for at least 1 day, though this can be extended to 4 or more days depending on the degree of sprouting required. This results in a vascular bed on a chip, which is ready to receive cells, cell aggregates, organoids, or other tissue.

Explant Tissue Preparation:

By way of example, mouse embryonic kidney rudiments are dissected from the embryo at the embryonic day 11. All of the dissection steps are performed in DMEM media supplemented with 1× penicillin/streptomycin, 25 mM HEPES and 10% FCS. In this method first a volume of between 20-30 µL of medium (culture medium: DMEM supplemented with 10% FCS, 1× glutamax, 1×1× penicillin/streptomycin) is dispensed onto the surface of the gel.

To transfer the kidney explant to the gel, a capillary micropipette can be used. This method of transferring tissue by pipetting will prevent tissue damage. Transferred tissue will sink to the bottom of the plate, in the centre of the gel inlet opening. If the position of the tissue is not centralised on the gel, a small and narrow needle (for example BD MicroFine 1 mL syringe) or fine forceps (for example Dumont #5) can be used to adjust the position by pushing the tissue to the desired position.

Explant-Vessel Co-Culture

Explant tissue can be positioned on top of the gel at day 0, or at any other day after induction of sprouting.

Explant tissue can be placed with tissue specific medium with or without a proangiogenic factor cocktail. Cells of the tissue in the absence of a proangiogenic cocktail in the co-culture might further attract sprouts, for example if the tissue itself is producing proangiogenic factors. In the situation in which the proangiogenic factors are added to the medium after placing of the explant in co-culture, these factors can stimulate vessels of the tissue Explants can be cultured and monitored every couple of days. Medium changes via the microchannels can be executed every day or every second day or even every third day. Optionally, only half of the medium can be changed at any one time, to avoid stressing the 30 cells in the co-culture that could be triggered by sudden changes in pH, osmolarity, oxygen tension etc during full volume medium change.

After a few hours in the cell culture device, the tissue attaches to the top of the gel, covering most of the gel surface. To preserve a tissue position, an overlay of ECM can be dispensed on top of the tissue (for example Collagen, Matrigel or fibrin gel mixed with medium can be used). For example: after initial 12-24 h of culture all medium is removed from medium channels. Matrigel is mixed with ice-cold medium to adjust to 1-5 mg/ml concentration of Matrigel. 20 μL of gel/medium mixture is dispensed on top of the tissue and incubated at 37° C. for 10 minutes. Then, an additional 30 μL of warm medium is dispensed on top of the Matrigel overlay.

The cell culture device now comprises an organoid, tissue explant or other biological tissue connected to a vascular network on a chip. The degree of vascularization can be monitored using microscopy, for example with fluorescently labelled endothelial cells, such as RFP-labelled HUVECs. The system produced by such methods is now ready for use in any desired assay, such as those described herein, in which the effect of a test compound on the tissue is to be investigated.

The above description is for the purpose of teaching the person of ordinary skill in the art how to practice the present invention, and it is not intended to detail all those modifications and variations which will become apparent upon reading the description. It is intended, however, that all such modifications and variations be included within the scope of the present invention, which is defined by the following claims.

The invention claimed is:

1. A cell culture device comprising a microfluidic network, the microfluidic network comprising:
   a microfluidic layer comprising a base, a microfluidic channel and a cover;
   an organoid compartment extending into the microfluidic layer through an aperture in the cover and in fluid communication with the microfluidic channel; and
   a first capillary pressure barrier substantially aligned with the aperture and dividing the microfluidic network into a first sub-volume comprising the organoid compartment and a second sub-volume comprising at least a part of the microfluidic channel.

2. The cell culture device according to claim 1, wherein the organoid compartment comprises a well having sidewalls that, in an in use orientation, extend vertically to the microfluidic layer.

3. The cell culture device according to claim 1, wherein the first capillary pressure barrier is located on the base of the microfluidic layer substantially opposite the aperture.

4. The cell culture device according to claim 1, wherein the first capillary pressure barrier defines at least in part a surface of the organoid compartment on the base of the microfluidic layer and is configured to confine a fluid to the first sub-volume.

5. The cell culture device according to claim 1, wherein the microfluidic network comprises a second capillary pressure barrier located on the base of the microfluidic layer substantially opposite and aligned with the aperture.

6. The cell culture device according to claim 5 wherein the second capillary pressure barrier further defines at least in part a surface of the organoid compartment on the base of the microfluidic layer.

7. The cell culture device according to claim 5, wherein the second capillary pressure barrier is concentric with the aperture and/or the first capillary pressure barrier.

8. The cell culture device according to claim 5, wherein the first and/or second capillary pressure barriers each span the complete width of the microfluidic channel and intersect on each end with sidewalls of the microfluidic channel.

9. The cell culture device according to claim 5, wherein the first capillary pressure barrier and/or the second capillary pressure barrier each independently comprise:
   a ridge of material protruding from an internal surface of the microfluidic channel;
   a groove in an internal surface of the microfluidic channel;
   a region of material of different wettability to an internal surface of the microfluidic channel; or
   a plurality of pillars at regular intervals.

10. The cell culture device according to claim 1, wherein the first capillary pressure barrier is concentric with the aperture.

11. A method for culturing cells or cell aggregates, comprising:
   a) introducing into the organoid compartment of a device of claim 1 a droplet of a gel or gel-precursor comprising one or more types of cells or cell aggregates;
   b) allowing the droplet to be confined by the first capillary pressure barrier;
   c) allowing the droplet of gel or gel-precursor to cure or gelate to form a cured or gelled gel;
   d) loading the microfluidic channel with a fluid; and
   e) culturing the one or more type of cells or cell aggregates present in the cured or gelled gel.

12. The method for culturing cells or cell aggregates according to claim 11, further comprising:
   f) inducing a flow of the fluid through the microfluidic network and/or
   g) introducing endothelial cells into the microfluidic channel.

13. The method for culturing cells or cell aggregates according to claim 12, further comprising stimulating the endothelial cells to form a layer of vascular tissue, wherein the layer of vascular tissue lines interior walls of the microfluidic channel to the interface of the cured gel.

14. The method for culturing cells or cell aggregates according to claim 11, further comprising:
   h) adding a chemoattractant, or one or more pro-angiogenic compounds, onto the cured or gelled gel or gel-precursor to promote directional angiogenesis within the cured or gelled gel.

15. The method for culturing cells or cell aggregates according to claim 11, further comprising culturing the one or more types of cells to form an organoid or an embryonic body.

16. A method of vascularising a cell aggregate, comprising:
- introducing into a microfluidic cell culture device according to claim 1 a droplet of a gel or gel-precursor and allowing the droplet to be confined by the first capillary pressure barrier present in the device;
- allowing the gel or gel-precursor to cure or gelate to form a cured or gelled gel;
- introducing a suspension of endothelial cells in a carrier fluid into a microfluidic channel of the microfluidic cell culture device, the microfluidic channel being in fluid communication with the cured or gelled gel;
- allowing the endothelial cells to form at least one microvessel in at least the microfluidic channel;
- introducing onto a top surface of the cured or gelled gel one or more cells or cell aggregates; and
- allowing or promoting directional angiogenesis between the at least one microvessel and the one or more cells or cell aggregates.

17. The method according to claim 16, further comprising:
- adding one or more pro-angiogenic compounds, onto the cured or gelled gel after formation of the at least one microvessel in at least the microfluidic channel to promote directional angiogenesis into the cured or gelled gel.

18. The method according to claim 16, wherein the one or more cells or cell aggregates comprise one or more of clustered cells, printed cells, an organoid, tissue biopsy, tumor tissue, resected tissue material, organ explant or an embryonic body.

19. The method according to claim 16, wherein introducing the one or more cells or cell aggregates comprises allowing the one or more cells or cell aggregates to fully cover the top surface of the cured or gelled gel as a monolayer or as a multi-layered tissue.

20. The method according to claim 16, further comprising introducing a further gel or gel-precursor into the microfluidic cell culture device so as to encapsulate the first cured or gelled gel and the one or more cells or cell aggregates.

* * * * *